United States Patent
Reddy et al.

(10) Patent No.: US 10,064,860 B2
(45) Date of Patent: Sep. 4, 2018

(54) **PHARMACEUTICAL COMPOSITIONS CONTAINING CLOFAZIMINE FOR INHIBITING *CLOSTRIDIUM DIFFICILE* ACTIVITY**

(71) Applicant: KamTek, Inc., Frederick, MD (US)

(72) Inventors: Venkata M. Reddy, Gaithersburg, MD (US); Wolf Prensky, Germantown, MD (US); Sharanjit VedBrat, Germantown, MD (US)

(73) Assignee: KamTek, Inc., Frederick, MD (US)

(*) Notice: Subject to any disclaimer, the term of this patent is extended or adjusted under 35 U.S.C. 154(b) by 0 days.

(21) Appl. No.: 15/831,237

(22) Filed: Dec. 4, 2017

(65) Prior Publication Data

US 2018/0092914 A1 Apr. 5, 2018

Related U.S. Application Data

(62) Division of application No. 15/421,982, filed on Feb. 1, 2017, now Pat. No. 9,849,130, which is a division of application No. 14/947,212, filed on Nov. 20, 2015, now abandoned.

(60) Provisional application No. 62/082,925, filed on Nov. 21, 2014, provisional application No. 62/133,058, filed on Mar. 13, 2015.

(51) Int. Cl.
| | |
|---|---|
| *A61K 31/498* | (2006.01) |
| *C07D 241/46* | (2006.01) |
| *A61K 31/7048* | (2006.01) |
| *A61K 38/14* | (2006.01) |
| *A61K 31/4164* | (2006.01) |
| *A61K 9/00* | (2006.01) |

(52) U.S. Cl.
CPC .......... *A61K 31/498* (2013.01); *A61K 9/0053* (2013.01); *A61K 31/4164* (2013.01); *A61K 31/7048* (2013.01); *A61K 38/14* (2013.01)

(58) Field of Classification Search
CPC ............................ A61K 31/498; C07D 241/46
USPC .......................................... 514/250; 544/348
See application file for complete search history.

(56) References Cited

U.S. PATENT DOCUMENTS

| | | |
|---|---|---|
| 2011/0240512 A1 | 10/2011 | Dorfner |
| 2012/0071472 A1 | 3/2012 | Liu et al. |
| 2013/0058983 A1 | 3/2013 | Baker |
| 2013/0231275 A1 | 9/2013 | Bushell et al. |

OTHER PUBLICATIONS

Hackam et al, "translation of Research Evidence from Animals to Humans," JAMA, 2006; 296(14):1731-1732.
International Search Report and Written Opinion dated, Feb. 2, 2016, in related International Patent Application No. PCT/US2015/061833, filed Nov. 20, 2015.
Jordan, V. C., "Tamoxifen: A Most Unlikely Pioneering Medicine," Nature Reviews: Drug Discovery, vol. 2 (2003) 205-212.
Wu et al., "The membrane as a target for controlling hypervirulent *Clostridium difficile* infections," J. Antimicrob. Chemother 68, pp. 806-815, 2013 (Advanced Access publication Dec. 21, 2012) [retrieved on Jan. 12, 2016]. Retrieved from the Internet: <URL: http://jac.oxfordjournals.org/content/68/4/806.full.pdf+html>.

*Primary Examiner* — Douglas M Willis
(74) *Attorney, Agent, or Firm* — Wiley Rein LLP

(57) ABSTRACT

Methods for inhibiting the activity of *Clostridium difficile* in a subject comprises administering to the subject a pharmaceutical composition consisting of clofazimine and at least one pharmaceutically acceptable excipient. Pharmaceutical compositions consisting of clofazimine at least one pharmaceutically acceptable excipient are provided for treating *Clostridium difficile* infection and diseases or symptoms associated therewith.

11 Claims, 7 Drawing Sheets

FIG. 1
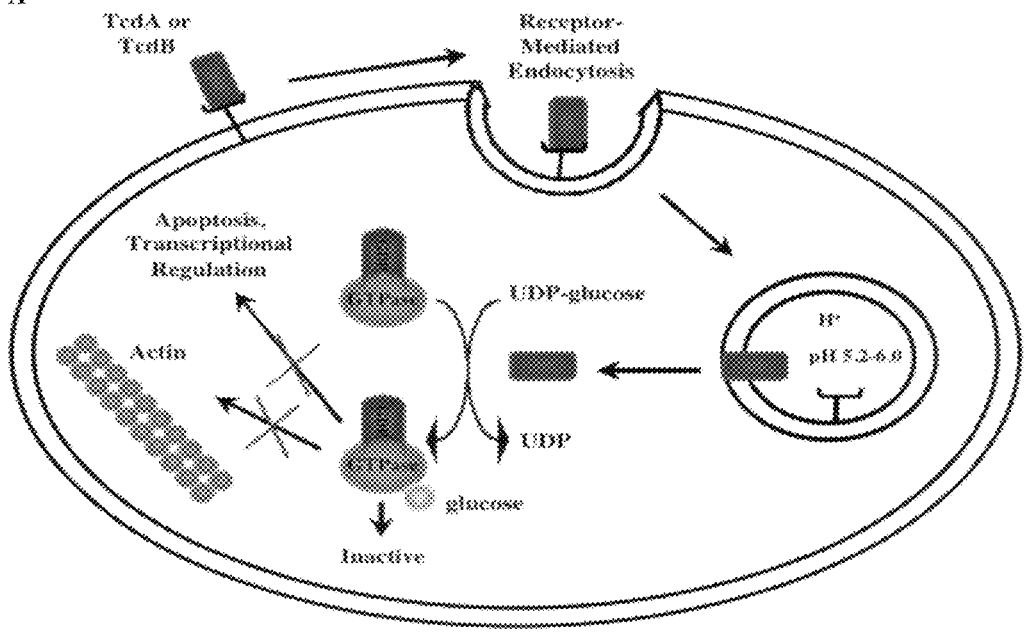
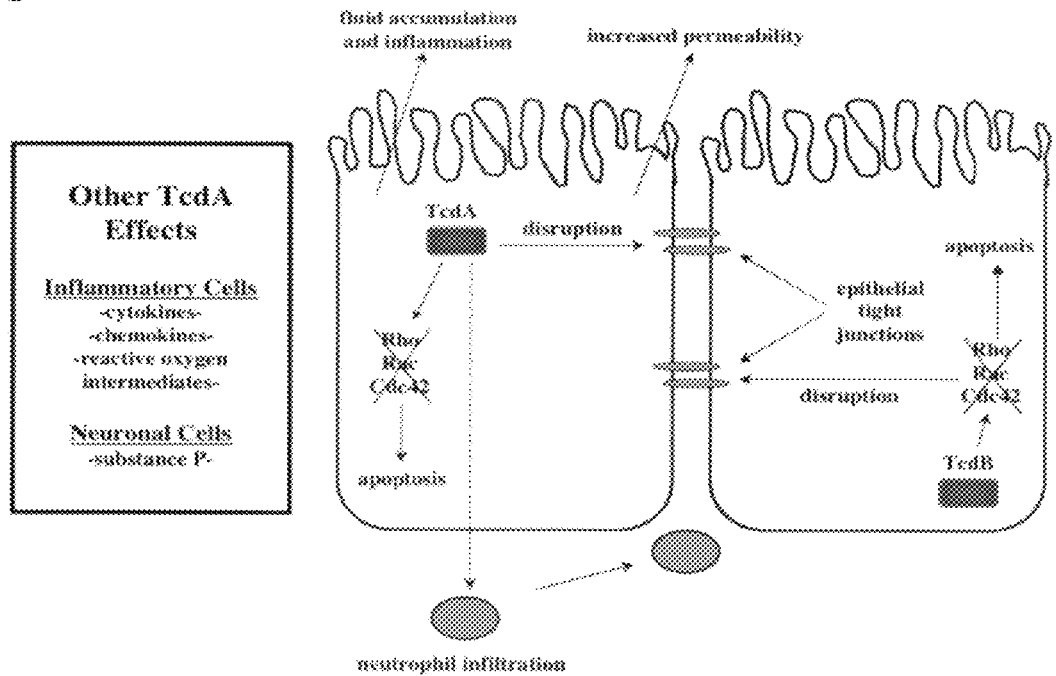

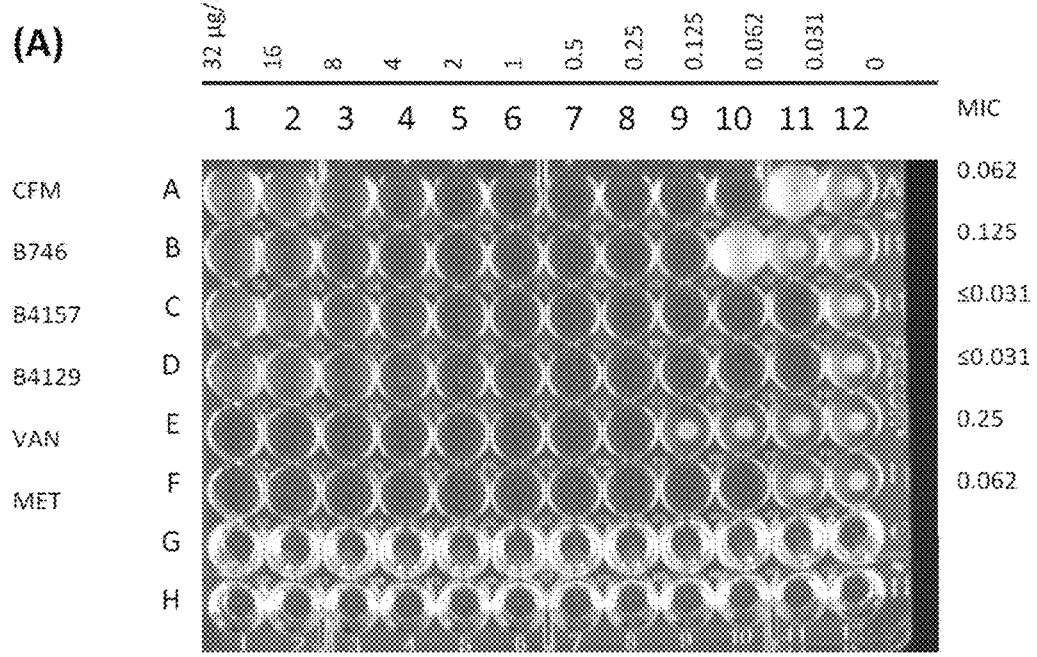
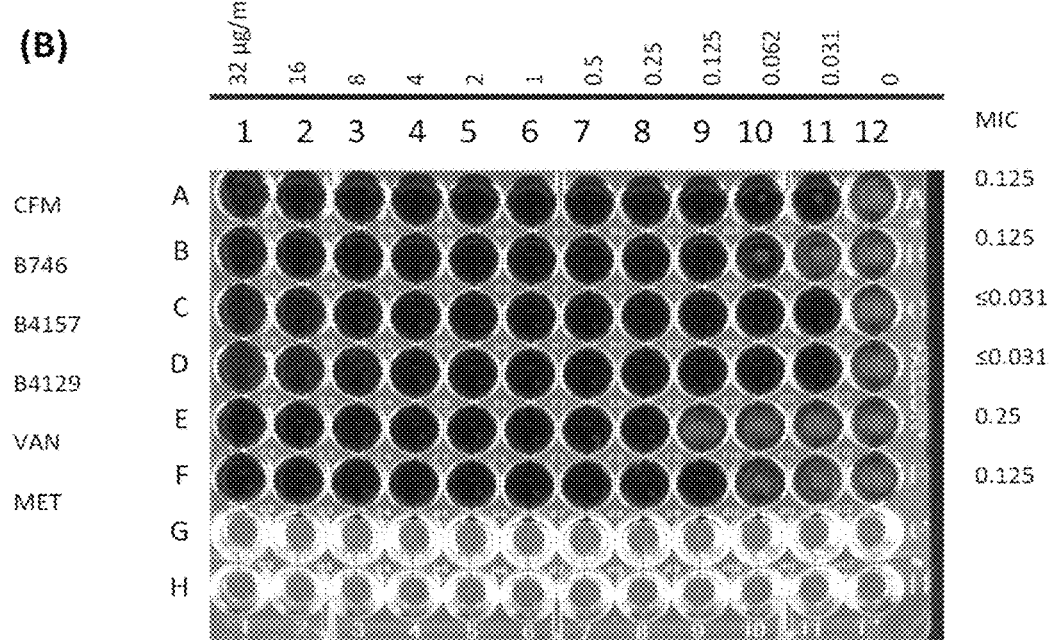
FIG. 4

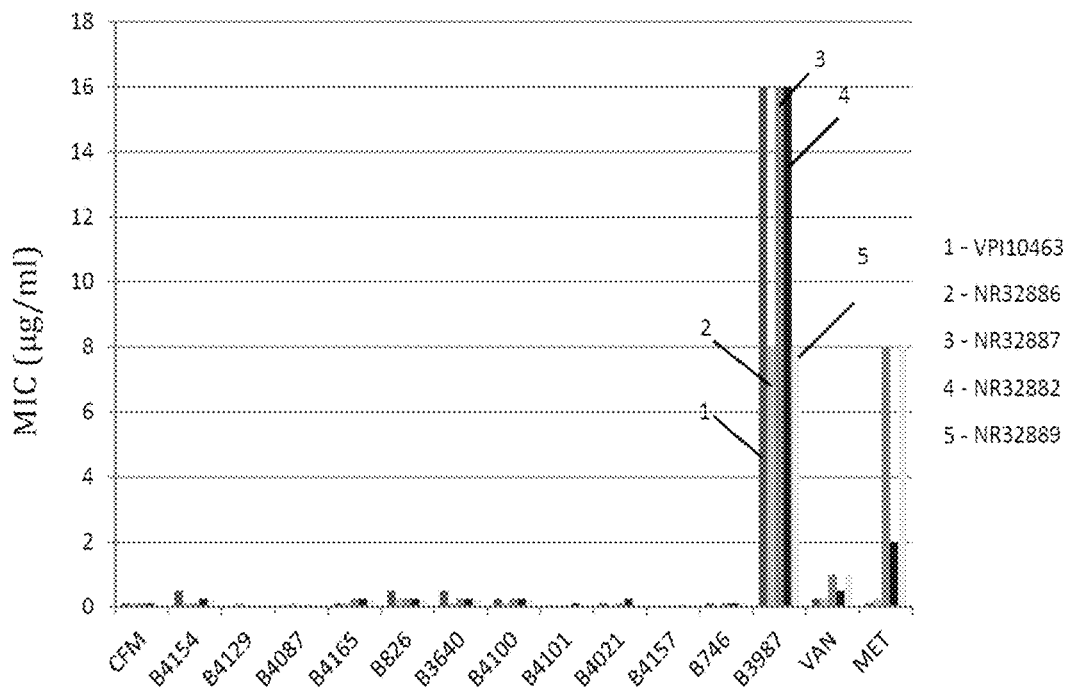
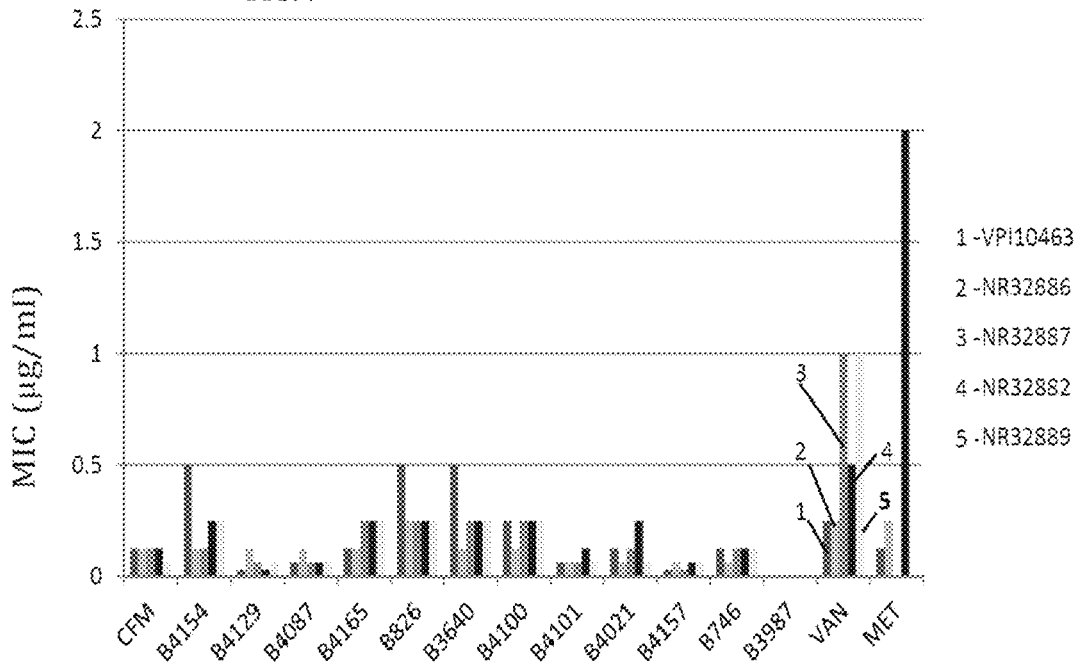

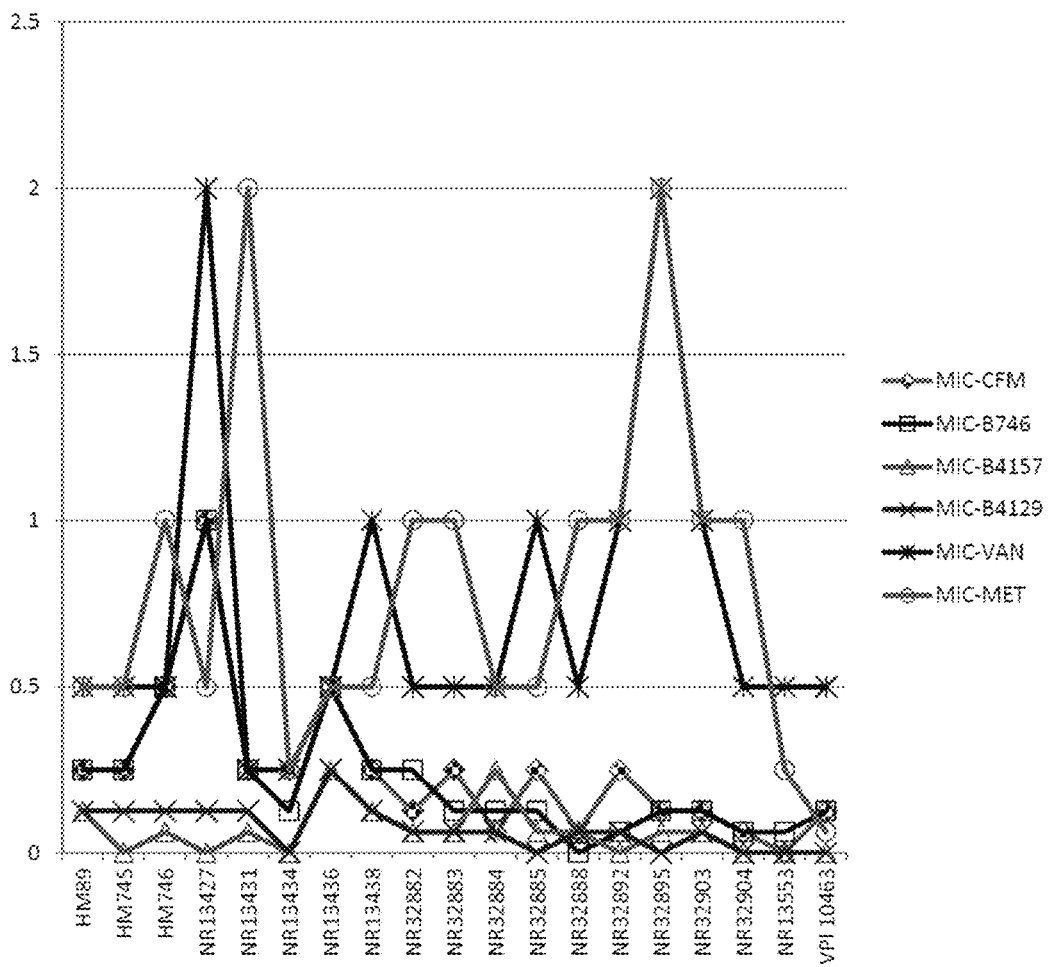

Fecal extracts of CFM formulations CFM

PHARMACEUTICAL COMPOSITIONS CONTAINING CLOFAZIMINE FOR INHIBITING *CLOSTRIDIUM DIFFICILE* ACTIVITY

CROSS REFERENCE TO RELATED APPLICATIONS

This Application is a divisional application of U.S. application Ser. No. 15/421,982, filed Feb. 1, 2017, which is a divisional application of U.S. application Ser. No. 14/947,212, filed Nov. 20, 2015, which claims priority benefit of U.S. Provisional Applications No. 62/082,925, filed Nov. 21, 2014, and No. 62/133,058, filed Mar. 13, 2015, which are incorporated herein by reference in their entireties for all purposes.

FIELD OF THE INVENTION

The present invention relates to methods for preventing or treating *Clostridium difficile* associated disease (CDAD), and in particular methods and compositions for treating CDAD by administering a therapeutically effective amount of clofazimine or analogues thereof, either alone or in combination with one or more additional therapeutic agents.

BACKGROUND OF THE INVENTION

*Clostridium difficile* (CD) is a Gram positive, spore-forming, anaerobic *bacillus* recognized to cause diarrhea, pseudomembranous colitis, toxic megacolon, other gastrointestinal conditions, and even death. Hedge et al. (2008) *New advances in the treatment of Clostridium difficile infection (CDI)*, Therapeutics and Clinical Risk Management 4(5):949-64; Tsutsumi et al. (2014) *Progress in the Discovery of Treatments for C. difficile Infection: A Clinical & Medicinal Chemistry Review*, Current Topics Med. Chem. 14:152-75. In its spore form, the bacterium is able to survive harsh environments and common sterilization techniques. Spores of CD are resistant to high temperatures, ultraviolet light, harsh chemicals, and many antibiotics, and remain viable for months or longer (Leffler & Lamont (2009) *Treatment of Clostridium difficile-Associated Disease*, Gastroenterol. 136:1899-1912).

Acquisition of CD occurs by ingestion of the acid-resistant spores, which pass through the stomach and germinate and inhabit the colon. In order for CD to overpopulate the colon, there is typically a disruption of the normal bacterial flora which otherwise provides colonization resistance to CD and other opportunistic pathogens. As such, the protection of normal gastrointestinal flora is an important defense to CD infection (CDI). Unfortunately, exposure to common antibiotic regimens (e.g., cephalosporins, penicillins and fluoroquinolones) in the course of medical treatment of infectious and other diseases (e.g., such as bowel surgery and/or cancer chemotherapy) disrupts the natural gut flora, allowing CD resistant to such antibiotics to colonize and overpopulate in the gut of some patients, particularly elderly patients.

Once colonized, CD reproduces and releases enterotoxin (toxin A or TcdA) and cytotoxin (toxin B or TcdB) in the colon. Tsutsumi, 2014; Heinlen & Ballard (2010) *Clostridium difficile Infection*, Am. J. Med. Sci. 340(3):247-52; Hedge et al., 2008. Both toxins A and B act as glucosyltransferases, inactivating small cellular GTPases (Rho, Rac & Cdc42), and triggering the attraction and adhesion of neutrophils resulting in inflammation of the mucosal lining, cellular necrosis, and increased peristalsis and capillary permeability, thereby degrading the colonic epithelial cells and leading to the clinical symptoms associated with CDI. Although both toxins are cytotoxic and stimulate apoptosis, toxin B is more potent while toxin A stimulates epithelial cell permeability and inflammatory response (effecting cytokine, chemokine and reactive oxygen intermediate production; neutrophil infiltration; mast cell accumulation; and substance P production, stimulating submucosal sensory neurons).

The mechanisms of action of CD toxins TcdA and TcdB are illustrated in FIG. 1, plates A and B. See Voth & Ballard (2005) *Clostridium difficile* Toxins: *Mechanisms of Action and Role in Disease*, Clin. Microbiol. Rev. 18(2):247-63. Clinical symptoms vary from asymptomatic colonization or mild diarrhea to life threatening illness, including severe inflammation, lesions and/or tissue necrosis of the gut mucosa. Typically, CDI-associated disease begins as watery diarrhea and progresses to pseudomembranous colitis. Distension of the colon may result in toxic megacolon. In addition, even cases of relatively mild CDI may rapidly progress to fulminant CDI, with such patients suffering systemic toxicity (e.g., leukocytosis, hypotension, renal failure, respiratory distress, or even death).

CD is a leading cause of hospital-acquired diarrhea, infections and other disease in Europe and North America. Heinlen & Ballard, 2010. Because of their increasing resistance to many common antibiotics, CD spores can remain in the gastrointestinal tract and potentially contribute to recurrent disease following conventional treatment regimens. As such, CD infections (CDIs) are increasing worldwide and have become more severe and refractory to treatment in the past decade. CDIs are one of the most common nosocomial infections in the United States, and presently, hospital-acquired CDIs exceed that of methicillin-resistant *Staphylococcus aureus* (MRSA) infections in some regions.

Increased incidence of hospital-associated CDI may be due to the utilization of a broad spectrum of antimicrobial agents to treat various other conditions. As such, the emergence of hypervirulent epidemic strains of CD (e.g., the fluoroquinolone resistant hypervirulent CD strain designated as NAP1/BI/027 in North America and Europe) produce increased amounts of toxins A and B, and thus exhibit increased rates of recurrence, morbidity and/or mortality (as compared to previously identified strains of CD), particularly in vulnerable elderly patients. For example, NAP1/BI/027 produces 16 times more toxin A and 23 times more toxin B compared to many conventional CD strains, and also produces an additional toxin known as binary toxin (see Hedge et al., 2008), which causes a 3-fold higher mortality rate as compared to patients infected with less virulent strains. Leffler & Lamont, 2009.

Effective treatment of CDI has proven to be quite challenging due to the need for selective eradication of CD without affecting the normal gut flora. After each episode or infection, the risk of recurrence of CDI generally increases. About 15%-30% of CDI patients get another infection after their first CDI, and about 40%-60% get a further CDI after their second episode of the infection. Tsutsumi et al., 2014. As such, for patients who experience two or more recurrences of symptomatic CDIs, a change in strategy is warranted. Leffler & Lamont, 2009.

Current therapies for CDI typically provide for the administration of antimicrobial agents including metronidazole (MET), vancomycin (VAN) or fidaxomicin (FDX). MET is the conventionally accepted agent for treating the first episode of CDI due to its relatively low cost, as well as concerns of emergence of VAN resistant *enterococci* (VRE) by extensive VAN treatment. See Leffler & Lamont, 2009. However, only VAN and FDX have been approved by the U.S. Food and Drug Administration (FDA) for the treatment of recurrent CDI. Moreover, use of VAN and FDX is relatively limited, particularly for treating the first episode of CDI, due to their relatively high cost (e.g., current cost is about $2000 per treatment).

Failure to respond to MET has become more common recently, and therefore VAN has become more commonly used as a first episode treatment, particularly in patients with more severe CDI. However, reports describing MET failures and questions of the equivalence of MET and VAN for CDI have been raised. Hedge et al., 2008.

Recurrence or failure rate associated with conventional MET, VAN and FDX treatments, as well as other conventional therapies, is relatively high. For example, between about 15% and about 30% of patients have a relapse of symptoms after successful initial treatment with such conventional treatments, usually within the first few weeks after treatment is discontinued Leffler & Lamont, 2009. Such relapse is sometimes due to the persistence of the same CD strain being treated, or alternatively or additionally due to reinfection with a new CD strain. With the emergence of hypervirulent epidemic strains of CD, recurrence rates of CDI have jumped to nearly 50% in patients treated with MET and VAN. The spectrum of activity for FDX is narrower compared to that of MET or VAN. However, efficacy of FDX is similar to that of VAN. When used to treat previous strains of CD, FDX exhibits a somewhat lower recurrence or failure rate as compared to MET and VAN. However, FDX exhibits no improvement in recurrence rates in patients infected with hypervirulent strains of CD (Louie et al. (2011) *Fidaxomicin versus vancomycin for Clostridium difficile infection*, N. Engl. J. Med. 364(5):422-31), and thus also exhibits recurrence rates of nearly 50%. As such, conventional FDX therapies have not proven to be effective for patients that have suffered multiple CDI relapses.

Thus, due to the increasing emergence of resistant and hyper-virulent CD strains and the high rate of recurrence of CDI after treatment with such conventional agents, there is an urgent need to develop new and better therapies. Alternative non-antibiotic based treatments for treating CDI have emerged, including fecal transplants and probiotics, which seek to restore or repopulate the normal gut flora. Other treatment methods, such as immunotherapy-based treatments and vaccines, attempt to neutralize the CD toxins or enhance the patient's immune response. However, such non-antibiotic based treatments have exhibited mixed results with less efficacy as compared to conventional microbial agents. As such, conventional treatments using MET, VAN and FDX remain prevalent.

Thus, new therapeutics and treatment methods are needed to improve efficacy and reduce failure and/or recurrence rates of CDIs. The ideal therapeutic agent would specifically eliminate or substantially reduce a CD population with minimal disturbance to normal gut flora. However, due to the exorbitant costs involved in the discovery and development of new agents, many pharmaceutical companies are reluctant to invest in new drug discoveries. Moreover, the return on investment for drug companies on short duration therapeutics like antimicrobial agents is not alluring compared to long duration or life-long therapies. Consequently, the discovery of new uses for previously known drugs (repurposing) is a very cost effective option. Indeed, the National Institutes of Health has an ongoing initiative in collaboration with pharmaceutical companies for discovering new therapeutic uses for existing molecules.

SUMMARY OF THE INVENTION

The present invention is directed to compositions and methods for treating CDI and/or CDAD. According to an embodiment of the present invention, a method of preventing or treating a subject infected with CD comprises administering to the subject a therapeutically effective amount of clofazimine (CFM) or a CFM derivative or analogue(s) including but not limited to B746, B4157, and B4129, either alone or in combination with one or more additional therapeutic agents. In some implementations, the compound is administered orally. In other implementations, the compound is administered parenterally. In some embodiments, for determining in vitro activity, the compound is administered in a concentration ranging from about 0.020 µg/ml to about 1.0 µg/ml, more preferably from about 0.031 µg/ml to about 0.25 µg/ml.

In some embodiments, the compound is administered in connection with a pharmaceutically acceptable carrier and/or excipient. In some implementations, a pharmaceutical composition suitable for administration in accordance with disclosed embodiments consists solely of a single active agent selected from the group consisting of CFM, and a CFM analogue including B746, B4157 and B4129. In other implementations, the pharmaceutical composition comprises CFM and/or a CFM analogue(s) including B746, B4157 and B4129, and/or one or more additional therapeutic agents (e.g., an antimicrobial agent, including but not limited to MET, VAN and/or FDX).

In one embodiment, a method of treating a subject infected with *Clostridium difficile* comprises administering to the subject a therapeutically effective amount of clofazimine or a clofazimine analogue. In some implementations, the clofazimine analogue is selected from the group consisting of B4154 analogue, B4129 analogue, B4087 analogue, B4165 analogue, B826 analogue, B3640 analogue, B4100 analogue, B4101 analogue, B4021 analogue, B4157 analogue, B746 analogue, and B3987 analogue. In preferred embodiments, the clofazimine analogue is B4129 analogue, B4157 analogue, or B746 analogue.

In some embodiments, the disclosed method provides for administering the compound orally. The compound may be administered in a concentration from about 0.020 µg/ml to about 1.0 µg/ml for in vitro conditions, more preferably in a concentration from about 0.031 µg/ml to about 0.25 µg/ml for in vitro conditions.

In some embodiments, the compound is administered in combination with at least one additional therapeutic agent. In some implementations, the additional therapeutic agent is an antimicrobial agent, including but not limited to vancomycin, metronidazole, or fidaxomicin.

In another embodiment, a method of treating a subject infected with a population of *Clostridium difficile* comprises administering to the subject a pharmaceutical composition comprising: (A) an effective amount of a first antimicrobial agent comprising clofazimine or a clofazimine analogue; (B) an effective amount of a second antimicrobial agent; and (C) a pharmaceutically acceptable carrier or excipient. The effective amounts of the first and second antimicrobial agents cause the pharmaceutical composition to mediate a synergistically increased reduction in the population of *Clostridium difficile* relative to the reductions in the population mediated by: (1) a pharmaceutical composition comprising said effective amount of said first antimicrobial agent but lacking said effective amount of said second antimicrobial agent; and (2) a pharmaceutical composition comprising said effective amount of said second antimicrobial agent but lacking said effective amount of said first antimicrobial agent.

In some embodiments, the pharmaceutical composition comprises a clofazimine analogue selected from the group consisting of B4154 analogue, B4129 analogue, B4087 analogue, B4165 analogue, B826 analogue, B3640 analogue, B4100 analogue, B4101 analogue, B4021 analogue, B4157 analogue, B746 analogue, and B3987 analogue. Preferably, the clofazimine analogue is B4129 analogue, B4157 analogue, or B746 analogue.

In some embodiments, the first antimicrobial agent is administered in a concentration from about 0.020 µg/ml to about 1.0 µg/ml for in vitro conditions, more preferably in a concentration from about 0.031 µg/ml to about 0.25 µg/ml for in vitro conditions.

In some embodiments, the second antimicrobial agent is selected from the group consisting of vancomycin, metronidazole, and fidaxomicin.

The present invention also relates to a pharmaceutical composition for killing or reducing a population of *Clostridium difficile* comprising a therapeutically effective amount of clofazimine or a clofazimine analogue, and a pharmaceutically acceptable carrier or excipient. The clofazimine analogue is preferably selected from the group consisting of B4154 analogue, B4129 analogue, B4087 analogue, B4165 analogue, B826 analogue, B3640 analogue, B4100 analogue, B4101 analogue, B4021 analogue, B4157 analogue, B746 analogue, and B3987 analogue. More preferably, the clofazimine analogue is B4129 analogue, B4157 analogue, or B746 analogue.

In some embodiments, the pharmaceutical composition also comprises at least one additional therapeutic agent. In some implementations, the additional therapeutic agent is an antimicrobial, an antibiotic, or a lytic enzyme. In some implementations, the additional therapeutic agent is an antimicrobial agent selected from the group consisting of vancomycin, metronidazole, and fidaxomicin.

The present invention also provides for use of the disclosed compounds comprising clofazimine and/or a clofazimine analogue(s), and/or use of the disclosed pharmaceutical composition(s) in the treatment or prevention of a disease or condition associated with *Clostridium difficile* infection.

BRIEF DESCRIPTION OF THE FIGURES

FIG. 1 illustrates schematically mechanisms of action of CD toxins. An overview of intracellular modifications by the CD toxins (TcdA and TcdB) is illustrated in plate A. TcdA and TcdB toxins enter the cell through receptor-mediated endocytosis and require an acidified endosome for translocation. The requirement for low pH is believed to be due to important structural changes which occur in the toxins, leading to exposure of hydrophobic domains prior to insertion into the target membrane. Both TcdA and TcdB act intracellularly as glycosyltransferases. Each toxin modifies and inactivates Rho, Rac, and Cdc42 via transfer of a sugar moiety, with UDP-glucose as a co-substrate. The effects of these modifications include actin condensation, transcriptional activation, and apoptosis. Downstream effects of TcdA and TcdB in intestinal cells during disease is shown in plate B. Exposure of intestinal epithelial cells to TcdA leads to neutrophil infiltration, substance P production, chemokine production, reactive oxygen intermediate production, disruption of tight junctions, and apoptosis. TcdB activity leads to disruption of tight junctions and apoptosis. A combination of one or more of these activities leads to fluid accumulation in the host and inflammatory responses.

FIG. 2 illustrates the chemical structures of: FIG. 2(a) Clofazimine; FIG. 2(b) B746 analogue; FIG. 2(c) B4157 analogue; and d) B4129 analogue.

FIG. 4 shows minimum inhibitory concentration (MIC) determinations by broth microdilution method against CD strain VPI 10463. Panel (A) depicts MIC results against CD strain VPI 10463 in brain heart infusion broth. Panel (B) depicts MIC results against CD strain VPI 10463 in brucella broth. The different drugs tested are identified along the left of panels (A) and (B) and presented in rows A-F (Row A, clofazimine (CFM); Row B, clofazimine analogue B746; Row C, clofazimine analogue B4157; Row D, clofazimine analogue B4129; Row E, vancomycin (VAN); Row F, metronidazole (MET); Rows G and H were empty. Different concentrations of the drugs are presented along the top of panels (A) and (B) and in Columns 1-11, with 32 µg/ml concentration in Column 1, with decreasing concentration in columns from left to right, to 0.031 µg/ml concentration in Column 11. A drug-free control is presented in Column 12. The minimal inhibitory concentration (MIC) [lowest concentration showing no sign of visible growth] of each drug is identified along the right of panels (A) and (B). MIC (µg/ml) results against the strain in brain heart infusion broth are as follows: CFM, 0.062; B746, 0.125; B4157, ≤0.031; B4129, ≤0.031; VAN, 0.25; and MET, 0.062. MIC (µg/ml) results against the strain in brucella broth are as follows: CFM, 0.125; B746, 0.125; B4157, ≤0.031; B4129, ≤0.031; VAN, 0.25; and MET, 0.125.

FIG. 6 illustrates graphically MIC (µg/ml) for 13 riminophenazine compounds against five CD strains, including CFM, 12 CFM analogues (B4154; B4129; B4087; B4165; B826; B3640; B4100; B4101; B4021; B4157; B746; and B3987), VAN and MET. Five bars above each compound tested represent, from left to right: strain 1 (VPI10463), strain 2 (NR32886), strain 3 (NR32887), strain 4 (NR32882) and strain 5 (NR32889), respectively (for example, such as identified above analogue B3987).

FIG. 7 illustrates graphically portions of MIC data shown in FIG. 6, with MIC data greater than 8 µg/ml removed in order to show MIC data≤2 µg/ml in further detail.

FIG. 8 illustrates graphically MIC (µg/ml) data for CFM, CFM analogues (B746, B4157, and B4129), VAN and MET against CD strains in brain heart infusion broth.

DETAILED DESCRIPTION OF THE INVENTION

The present invention is directed to pharmaceutical compositions and methods for preventing or treating CDI and/or CDAD. According to embodiments of the present invention, pharmaceutical compositions for treating CDI and/or CDAD comprise clofazimine (CFM) and/or a CFM analogue(s), either as the primary or sole active compound or in combination with one or more additional therapeutic agents. According to other embodiments, pharmaceutical compositions for treating CDI and/or CDAD additionally or alternatively comprise azaquinone (AZQ) (also known as Gangamicin, NSC 186017, and BRN 0407295).

Figure 2:
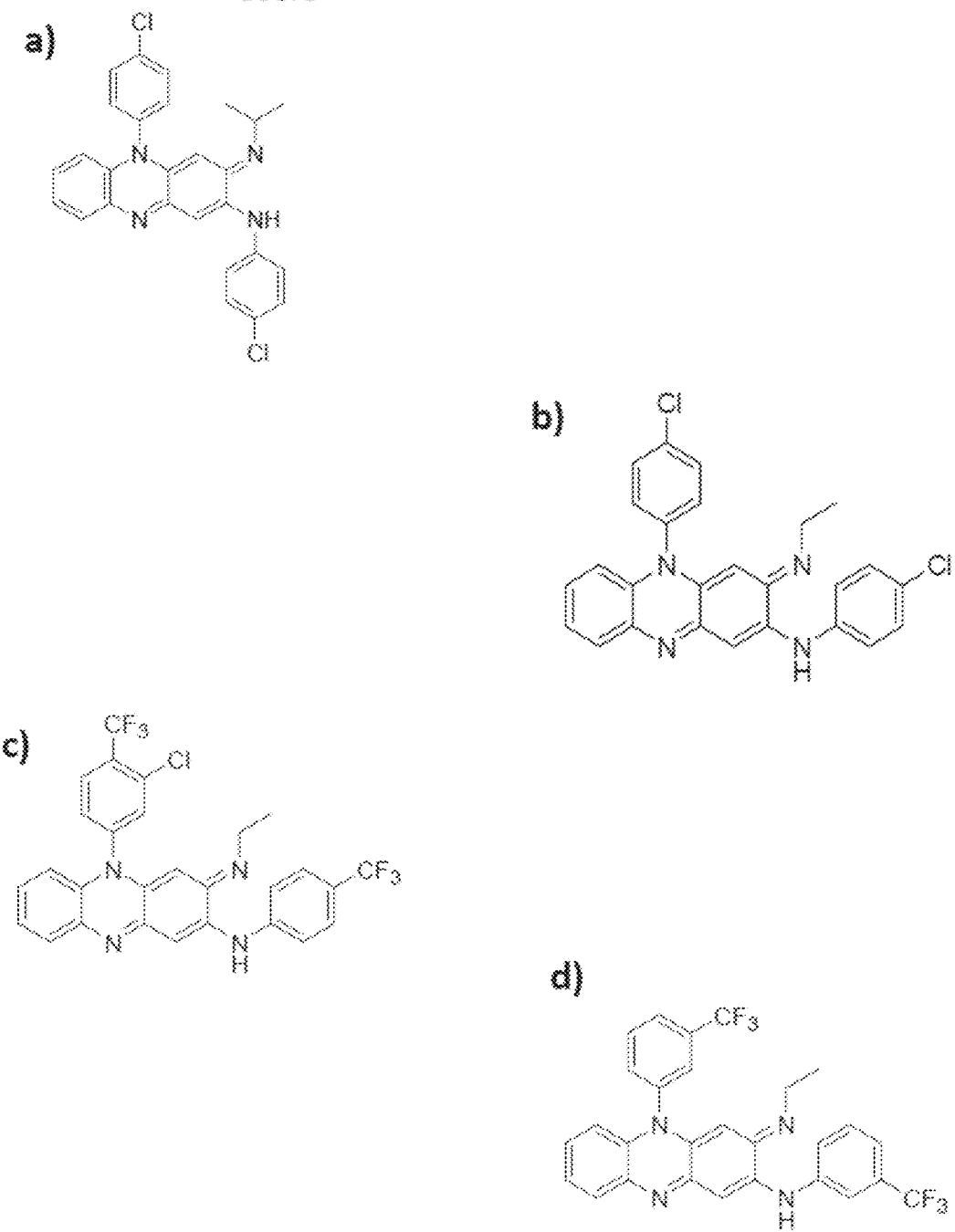

CFM (see FIG. 2(a)), 3-(p-chloroanilino)-10-(p-chlorophenyl)-2,10-dihydro-2-iso-propyliminophenazine, is a fat-soluble riminophenazine dye, which was discovered and developed as a treatment for tuberculosis (TB) in the 1950s. However, because of its low activity against TB in guinea pig and simian models, the interest in the drug as an effective treatment for TB quickly diminished, although CFM continues to be used for treating multidrug resistant TB. See Cholo et al. (2011) *Clofazimine: current status and future prospects*, J. Antimicrob. Chemother. 67:290-98.

In addition, in its micronized form, CFM was discovered to be effective against leprosy. Since then, it has continued to be used for treating multibacillary leprosy in a multidrug regimen consisting of dapsone, rifampin and CFM (Reddy et al. (1999) *Antimycobacterial activities of riminophenazines*, J. Antimicrob. Chemother. 43:615-23), and has been particularly effective for treating immune mediated conditions (e.g., erythema nodosum leprosum (ENL), *Mycobacterium avium* complex (MAC) disease, rhinoscleroma, pyoderma gangrenosum, necrobiosis lipoidica, severe acne, pustular psoriasis, and lupus erythematosus). CFM has also been used effectively in the treatment of Crohn's disease. Feller et al. (2010) *Long-Term Antibiotic Treatment for Crohn's Disease: Systematic Review and Meta-Analysis of Placebo-Controlled Trials*, Clin. Infect. Dis. 50:473-80). However, anaerobic bacteria (such as CD) have not been implicated in the pathogenesis of Crohn's disease. Id.

CFM is believed to kill bacteria by disruption or destabilization of bacteria membrane function. In particular, CFM selectively accumulates in bacterial membranes and stimulates reactive oxygen species, blocks $K^+$ channels and/or enhances bacterial phospholipase $A_2$ activity and the release of lysophospholipids. CFM is virtually insoluble in water (solubility 0.225 mg/L). It has an orally absorbed bioavailability of between about 45% and 65%. CFM has a half-life of about 10 days after a single dose of 100 mg, and about 70 days following long-term high dosage of 300 mg. For example, recommended dosage of CFM for treating leprosy is between 100-300 mg daily for 2-3 years in combination with other antileprosy drugs (dapsone and rifampin). CFM exhibits low plasma concentration, but relatively high tissue concentration. CFM is highly lipophilic and deposits primarily in fatty tissues and the reticuloendothelial system throughout the body. It is metabolized in the liver forming three metabolites, and excreted mainly in the feces, although it is detectable in all body secretions.

Various adverse effects associated with treatment of leprosy and TB using CFM have been reported (Reddy et al., 1999) including: skin pigmentation (approximately 75-100% of patients); icthyosis and dryness of skin (approximately 8-28% of patients), rash and pruritus (approximately 1-5% of patients); gastrointestinal conditions including abdominal and epigastric pain, nausea, vomiting and/or diarrhea (approximately 40-50% of patients); ocular conditions including conjunctival pigmentation, itching and dryness (approximately 1% of patients). Such adverse effects are typically reported, if at all, after several weeks of treatment, and are generally reversible and dissipate upon cessation of treatment.

In accordance with disclosed embodiments, the duration of treatment for CD is significantly shorter (e.g., 7-10 days) as compared to the duration of treatment for leprosy, TB or other chronic diseases wherein CFM is used. The possibility of such reported adverse effects associated with CFM are therefore minimized or eliminated when used in accordance with disclosed embodiments of treatment.

Compositions and methods utilizing or including CFM and/or CFM analogues are effective in killing or reducing CD populations and in particular for treating CDI and/or CDAD. In some implementations, pharmaceutical compositions include CFM and/or a CFM analogue(s) as the primary or sole active ingredient(s) or compound. In other implementations, pharmaceutical compositions include CFM and/or a CFM analogue(s) in combination with one or more additional therapeutic agents.

As demonstrated, the disclosed compounds exhibit excellent in vitro activity against CD. In vitro activity of antimicrobial agents may be expressed in terms of a minimal inhibitory concentration (MIC), which is considered to be the lowest concentration effective in preventing further bacterial growth, or killing or substantially reducing a bacterial population. $MIC_{50}$ represents the MIC of the active compound(s) effective against 50% of tested isolates; $MIC_{90}$ represents the MIC of the active compound(s) effective against 90% of tested isolates.

Figure 3:
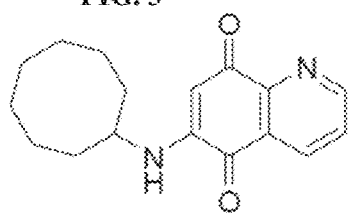
FIG. 3 illustrates the chemical structure of azaquinone.

In accordance with disclosed embodiments, AZQ also exhibited excellent in vitro activity against CD, and is thus demonstrated herein to be an effective bactericidal specific for CD treatment and/or for use in pharmaceutical compositions for treating CDI and/or CDAD. AZQ (FIG. 3), 6-(cyclooctylamino)-5, 8-quinolinequinone (CQQ) is an analogue of the ubiquinone (co-enzyme Q) and acts as an inhibitor of the cell-wall synthetic process. AZQ is known to be active against *M. tuberculosis* and *M. avium*. Hart et al. (1996) *Tuberculosis into the next century*, J. Med. Microbiol. 44:1-34; U.S. Pat. No. 4,963,565. Chemical and physical properties of AZQ are presented in Table 1 below:

TABLE 1

| AZQ Properties | |
|---|---|
| Molecular Weight | 284.3529 g/mol |
| Molecular Formula | $C_{17}H_{20}N_2O_2$ |
| XLogP3 | 3.8 |
| Hydrogen Bond Donor Count | 1 |
| Hydrogen Bond Acceptor Count | 4 |
| Rotatable Bond Count | 2 |
| Tautomer Count | 3 |
| Exact Mass | 284.152478 g/mol |
| Monoisotopic Mass | 284.152478 g/mol |
| Topological Polar Surface Area | 59.1 $A^2$ |
| Heavy Atom Count | 21 |
| Formal Charge | 0 |
| Complexity | 436 |
| Isotope Atom Count | 0 |
| Defined Atom Stereocenter Count | 0 |
| Undefined Atom Stereocenter Count | 0 |
| Defined Bond Stereocenter Count | 0 |
| Undefined Bond Stereocenter Count | 0 |
| Covalently-Bonded Unit Count | 1 |
| Feature 3D Acceptor Count | 3 |
| Feature 3D Donor Count | 1 |
| Feature 3D Cation Count | 1 |
| Feature 3D Ring Count | 2 |
| Effective Rotor Count | 3.6 |
| Conformer Sampling RMSD | 0.6 |
| CID Conformer Count | 53 |

In accordance with disclosed embodiments, methods of treating a subject (e.g., a mammal such as a human) infected with CD provide for administering to such subject a therapeutically effective amount of CFM, a CFM analogue (e.g., B746, B4157, B4129), and/or AZQ. In some implementations, the subject is administered a pharmaceutical composition comprising CFM, a CFM analogue(s), and/or AZQ, optionally one or more additional therapeutic agents, and a pharmaceutically acceptable carrier and/or excipient. Such composition(s) may be administered to the subject using an administration technique known to those of skill in the art (e.g., orally or intravenously), as discussed in further detail below.

The present invention provides for pharmaceutical compositions containing therapeutically effective amounts of CFM and/or a CFM analogue(s). The pharmaceutical compositions of the present invention may include a secondary therapeutic agent in addition to therapeutically effective amounts of CFM and/or a CFM analogue(s), such as for example an additional antimicrobial, antibiotic, and/or lytic enzyme. The pharmaceutical compositions may be formulated with pharmaceutically acceptable carriers or diluents as well as any other known adjuvants and excipients in accordance with conventional techniques such as those disclosed in REMINGTON: SCI. & PRACTICE OF PHARM., 21th Edition, Gennaro, Ed., Mack Publishing Co., Easton, Pa., 2005.

The pharmaceutically acceptable carriers or diluents, as well as any other known adjuvants and excipients, e.g., such as preservatives, wetting agents, emulsifying agents, dispersing agents, preservatives or buffers, may enhance shelf life or effectiveness of the pharmaceutical composition. Such carriers, diluents and/or other adjuvants should be suitable for the chosen compound(s) of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)).

The pharmaceutical compositions of the present invention may thus include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in the composition. The diluent is selected to not affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

Pharmaceutically acceptable carriers include any and all suitable solvents, dispersion media, coatings, antibacterial agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts and may alternatively or additionally be included.

The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable or biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., SUSTAINED & CONTR. RELEASE DRUG DELIV. SYS. (J. R. Robinson, ed., Marcel Dekker, Inc., New York, 1978).

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Pharmaceutical compositions of the present invention may also comprise isotonicity agents, such as sugars, polyalcohols, such as mannitol, sorbitol, glycerol or sodium chloride.

In one embodiment, the compounds of the present invention may be formulated to ensure proper distribution and efficacy in vivo. Pharmaceutically acceptable carriers for parenteral administration may include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound(s), use thereof in the pharmaceutical compositions of the present invention is contemplated.

Pharmaceutical compositions for injection must typically be sterile and stable under the conditions of manufacture and storage. The compositions may be formulated as a solution, microemulsion, liposome, or other ordered structure suitable to high drug concentration. The carrier may be a aqueous or nonaqueous solvent or dispersion medium containing for instance ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In some cases, it will be preferable to include isotonic agents, for example, sugars, polyalcohols such as glycerol, mannitol, sorbitol, or sodium chloride in the composition.

Prolonged absorption of the compositions may be brought about by including in the composition an agent that delays absorption, for example, monostearate salts and gelatin. Sterile solutions may be prepared by incorporating the active compound in the required amount in an appropriate solvent with one or a combination of ingredients, e.g., as enumerated above, as required, followed by sterilization microfiltration. Generally, dispersions are prepared by incorporating the active compound into a sterile vehicle that contains a basic dispersion medium and the required other ingredients, e.g., from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The pharmaceutical compositions may be prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Methods of treating CDI and/or CDAD in a patient in accordance with the present invention comprise administering to the patient a therapeutically effective amount of CFM and/or a CFM analogue(s), either alone or in combination with one or more additional therapeutic agents as noted above. The term "treat" or "treating" a disease, including an infectious disease or infection, refers to killing or reducing the growth of the bacteria (e.g., CD) causing such disease or infection, and/or reducing, ameliorating or eliminating symptoms associated with such disease or infection. A "therapeutically effective amount" refers to an amount of active compounds (e.g., CFM, CFM analogue(s) and/or one or more additional therapeutic agents) sufficient to elicit a desired biological response in a subject, and in particular an amount sufficient to kill, reduce or stabilize a bacterial population causing an infection or related disease and/or sufficient to reduce symptoms associated with such infection or disease. Preferably, a therapeutically effective amount of the active compounds of the present invention is effective in reducing growth of the bacterial population by at least about 50%, more preferably by at least about 75%, most preferably by at least about 90% or more.

In some embodiments, a method of treating or preventing CDI and/or CDAD provides for administering to a subject a pharmaceutical composition comprising CFM, a CFM analogue(s) and/or AZQ, along with one or more additional therapeutic agents, such as an additional antimicrobial agent (e.g., FDX, VAN or MET), an antibacterial, an antibody, a cell binding motif, or an antibiotic.

The efficacy of the disclosed pharmaceutical compositions and methods herein may be enhanced if more of the active compounds remain in the gut (as opposed to absorbing into the bloodstream). In some embodiments, the disclosed compounds and pharmaceutical compositions may be administered to a subject on an empty stomach (e.g., ½ hour, more preferably 1-2 hours, before or after ingesting any food or drinks, excluding water).

Dosage regimens in the above methods of treatment and uses are adjusted to provide the optimum desired response (e.g., a therapeutic response). For example, a single bolus may be administered, several divided doses may be administered over time, or the dose may be proportionally reduced or increased as indicated by the exigencies of the therapeutic situation. Pharmaceutical compositions may be formulated in dosage unit form for ease of administration and uniformity of dosage. Dosage unit form as used herein refers to physically discrete units suited as unitary dosages for the patients to be treated, with each unit containing a predetermined quantity of active compound calculated to produce the desired therapeutic effect in association with the required pharmaceutical carrier. The specification for the dosage unit forms of the present invention are dictated by and dependent on the characteristics of the active compound and the particular therapeutic effect to be achieved, as well as any limitations in the art of compounding such an active compound for the treatment of sensitivity in individuals.

A physician having ordinary skill in the art may readily determine and prescribe the therapeutically effective amount of the pharmaceutical composition required for a particular patient. The actual dosage levels of the active ingredient(s) in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known to those in the medical arts.

In addition, the therapeutically effective amount is one in which any toxic or detrimental effects of the pharmaceutical composition are outweighed by the therapeutically beneficial effects. The physician may start doses of pharmaceutical compositions comprising the active compounds of the present invention at levels lower than that required in order to achieve the desired therapeutic effect and gradually increase the dosage until the desired effect is achieved. In general, a suitable daily dose of a composition of the present invention will be that amount of the compound which is the lowest dose effective to produce the desired therapeutic effect (e.g., killing or reducing a population of CD bacteria), and/or for treating or preventing infection, and/or for ameliorating or alleviating symptoms associated with such bacteria in a subject). Such an effective dose will generally depend upon the factors described above.

While it is possible for a compound of the present invention to be administered alone, it is preferable to administer the compound(s) as a pharmaceutical composition as described above. The pharmaceutical compositions of the present invention may be administered by any suitable route and mode, including: parenteral, topical, oral or intranasal for prophylactic and/or therapeutic treatment. In one embodiment, a pharmaceutical composition of the present invention is administered orally. In another embodiment, a pharmaceutical composition of the present invention is administered parenterally. The phrases "parenteral administration" and "administered parenterally" as used herein means modes of administration other than enteral and topical administration, usually by injection (e.g., including epidermal, intravenous, intramuscular, intraperitoneal, subcutaneous, etc.). Additional suitable routes of administering a compound of the present invention in vivo and in vitro are well known in the art and may be selected by those of ordinary skill in the medical arts. The pharmaceutical compositions and compounds in accordance with the present invention may be administered via capsules, tablets, lozenges, chewing gums, powders, sprays, liquids, ointments, etc.

Although some embodiments are described with respect to use in humans, the pharmaceutical compositions and methods of the present invention are also suitable for veterinary (non-human) applications. For example, studies have isolated CD from meat products intended for consumption by humans or pets. See Songer et al. (2009) *Clostridium*

*difficile* in retail meat products, *USA*, 2007, Emerg. Infect. Dis. 15(5):819-21. The pharmaceutical compositions and compounds of the present invention may be utilized for treating bacterial infection or contamination in livestock or other animals (e.g., by administration to such livestock or animal orally, nasally, parenternally, onto the skin or coat, via intramammary infusion, teat dip, etc. as described herein).

Additional characteristics and features of the present invention will be further understood through reference to the following additional discussion and examples, which are provided by way of further illustration and are not intended to be limiting of the present invention.

Minimal Inhibitory Concentration Screenings:

In initial screenings, minimum inhibitory concentration (MIC) of CFM and CFM analogues (the test compounds) were determined by broth microdilution method in two different media, brucella broth (BB) and brain heart infusion broth (BHI), wherein serial dilutions of the test compounds were prepared in 100 µl volumes of BB/BHI broth in 96-well microtiter plates. BB and BHI are suitable for the cultivation of most anaerobic bacteria and other fastidious microorganisms; however, BB including lysed blood cells provides data in test environment much closer to in vivo conditions as compared to BHI test data.

Figure 5:
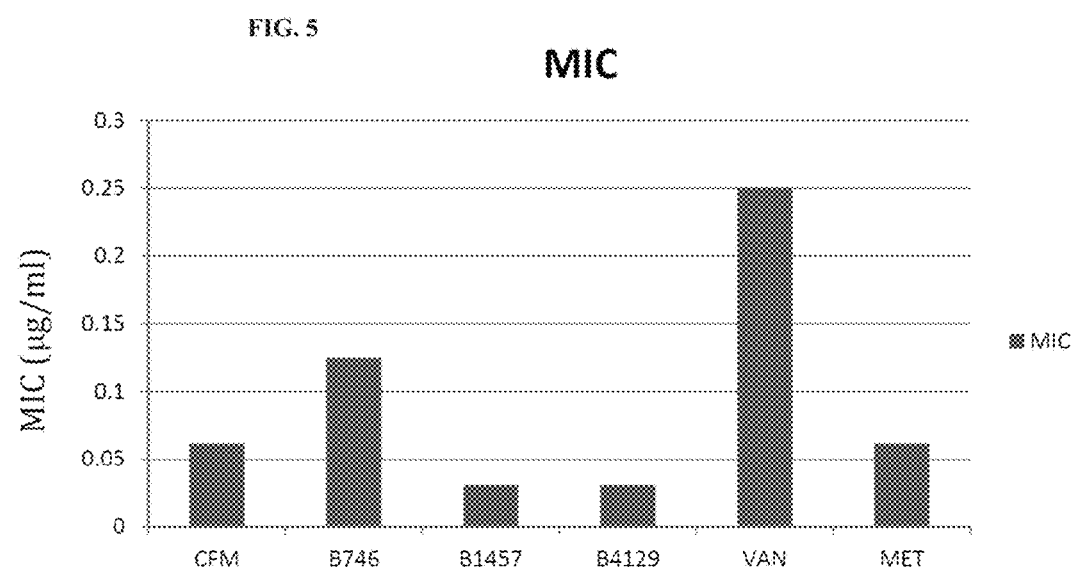
FIG. 5 illustrates graphically MIC determinations presented in FIG. 4.

Referring to FIG. 4 and FIG. 5, MIC was determined for CFM, analogues B746, B4157 and B4129, as well as VAN and MET by broth microdilution method against CD strain VPI-10463. MIC results in BHI are shown in FIG. 4, panel (A). MIC results in BB are shown in FIG. 4, panel (B).

The drug dilutions were kept in the Bactron EZ anaerobic chamber (Shel Lab., Cornelius, Oreg.) for 4-6 hours to reduce. Overnight growth of CD strains in BHI were adjusted to 0.1 OD at λ600, diluted 1:20 in BB/BHI, and 100 µl volumes were dispensed to each well. Positive controls of VAN and MET were run in parallel with each test. The microtiter plates were placed in zip-lock bags and left in the anaerobic chamber at 37° C. for 48 hours before reading. The lowest concentration at which each test compound showed no visible growth was determined to be the MIC. (The MIC of the test compounds against aerobic bacteria was also determined by broth microdilution method in Muller-Hinton broth using the same protocol).

With continued reference to FIG. 4, panels (A) and (B), each row contains a tested drug: row A, clofazimine (CFM); row B, clofazimine analogue B746; row C, analogue B4157; row D, analogue B4129; row E, vancomycin (VAN); row F, metronidazole (MET). Rows G and H were empty (not used). The tested drugs were diluted in culture medium from left to right; thus, each column of wells contained a different concentration of the drug starting from 32 µg/ml in column 1 (the left most column), 16 µg/ml in column 2, and so forth, through 0.031 µg/ml in column 11. Column 12 (the right most column) was a drug-free control. Addition of bacteria to each well of the plates and their incubation for 48 hours was under anaerobic conditions. At the end of incubation, clear wells indicated no visible bacteria growth, while white or gray deposits in the wells indicated growth (see FIG. 4, panels (A) and (B)).

The lowest concentration of the drug showing no visible growth was determined to be MIC. As shown in FIG. 4, panel (A), row A containing CFM, wells in columns 1 through 10 indicate no visible growth, while the well in column 11 shows visible CD growth. Thus, the well in column 10 containing 0.062 µg/ml had the lowest concentration of CFM showing no visible bacterial growth—therefore, MIC of CFM was considered to be 0.062 µg/ml in BHI (panel (A)).

MIC of CFM against various tested CD strains ranged from ≤0.031 to 0.25 µg/ml, with $MIC_{50}$ determined to be 0.062 µg/ml and $MIC_{90}$ determined to be 0.25 µg/ml. CFM demonstrated relatively low activity against other Gram-positive bacteria tested as presented below (e.g., *Enterococcus faecalis*, *Enterococcus faecium*, and *Staphylococcus aureus*), and was not active against aerobic Gram-negative bacteria tested (e.g., *Escherichia coli*). As such, CFM and particular analogues of CFM demonstrated effective bactericidal activity against and specific for CD.

CFM and Analogue Activity Against CD Strains:

Thirteen riminophenazine compounds, including CFM and 12 CFM analogues (B4154, B4129, B4087, B4165, B826, B3640, B4100, B4101, B4021, B4157, B746, B3987), as well as VAN and MET, were screened to determine activity against five CD strains. Twelve out of thirteen riminophenazines demonstrated good activity with MICs of ≤0.5 µg/ml, as shown in Table 2 and graphically in FIG. 6 and FIG. 7.

TABLE 2

MIC of CFM and CFM Analogues against CD strains

| | MIC (µg/ml) against CD strain | | | | |
|---|---|---|---|---|---|
| Analog: | VPI10463 | NR32886 | NR32887 | NR32882 | NR32889 |
| CFM | 0.125 | 0.125 | 0.125 | 0.125 | 0.062 |
| B4154 | 0.5 | 0.125 | 0.125 | 0.25 | 0.25 |
| B4129 | ≤0.031 | 0.125 | 0.062 | ≤0.031 | 0.062 |
| B4087 | 0.062 | 0.125 | 0.062 | 0.062 | 0.062 |
| B4165 | 0.125 | 0.125 | 0.25 | 0.25 | 0.25 |
| B826 | 0.5 | 0.25 | 0.25 | 0.25 | 0.25 |
| B3640 | 0.5 | 0.125 | 0.25 | 0.25 | 0.25 |
| B4100 | 0.25 | 0.125 | 0.25 | 0.25 | 0.25 |
| B4101 | 0.062 | 0.062 | 0.062 | 0.125 | 0.062 |
| B4021 | 0.125 | 0.062 | 0.125 | 0.25 | 0.062 |
| B4157 | ≤0.031 | 0.062 | ≤0.031 | 0.062 | 0.062 |
| B746 | 0.125 | 0.062 | 0.125 | 0.125 | 0.125 |
| B3987 | 16 | 8 | 16 | 16 | 8 |
| VAN | 0.25 | 0.25 | 1 | 0.5 | 1 |
| MET | 0.125 | 0.25 | 8 | 2 | 8 |

BB = *Brucella* broth;
BHI = brain heart infusion;
CFM = clofazimine;
VAN = vancomycin;
MET = metronidazole;
the rest are CFM analogs Following the initial screen of the 13 riminophenazine compounds (Table 2), four compounds (CFM, and CFM analogues B746, B4157, and B4129) were selected for further testing against a panel of additional CD strains. MIC data for CFM and analogues B746, B4157 and B4129 against various CD strains in BHI, as well as MICs for VAN and MET, were determined, as presented in Table 3 and graphically in FIG. 8.

TABLE 3

MIC of CFM and CFM Analogues against CD strains in BHI

| | MIC (µg/ml) | | | | | |
|---|---|---|---|---|---|---|
| Strain: | CFM | B746 | B4157 | B4129 | VAN | MET |
| HM89 | 0.25 | 0.25 | 0.125 | 0.125 | 0.5 | 0.5 |
| HM745 | 0.25 | 0.25 | ≤0.031 | 0.125 | 0.5 | 0.5 |
| HM746 | 0.5 | 0.5 | 0.062 | 0.125 | 0.5 | 1 |

TABLE 3-continued

MIC of CFM and CFM Analogues against CD strains in BHI

| Strain: | CFM | B746 | B4157 | B4129 | VAN | MET |
|---|---|---|---|---|---|---|
| NR13427 | 1 | 1 | ≤0.031 | 0.125 | 2 | 0.5 |
| NR13431 | 0.25 | 0.25 | 0.062 | 0.125 | 0.25 | 2 |
| NR13434 | 0.25 | 0.125 | ≤0.031 | ≤0.031 | 0.25 | 0.25 |
| NR13436 | 0.5 | 0.5 | 0.25 | 0.25 | 0.5 | 0.5 |
| NR13438 | 0.25 | 0.25 | 0.125 | 0.125 | 1 | 0.5 |
| NR32882 | 0.125 | 0.25 | 0.062 | 0.062 | 0.5 | 1 |
| NR32883 | 0.25 | 0.125 | 0.062 | 0.062 | 0.5 | 1 |
| NR32884 | 0.062 | 0.125 | 0.25 | 0.062 | 0.5 | 0.5 |
| NR32885 | 0.25 | 0.125 | 0.062 | ≤0.031 | 1 | 0.5 |
| NR32888 | 0.062 | ≤0.031 | 0.062 | 0.062 | 0.5 | 1 |
| NR32892 | 0.25 | 0.062 | ≤0.031 | 0.062 | 1 | 1 |
| NR32895 | 0.125 | 0.125 | 0.062 | ≤0.031 | 2 | 2 |
| NR32903 | 0.125 | 0.125 | 0.062 | 0.062 | 1 | 1 |
| NR32904 | 0.062 | 0.062 | ≤0.031 | ≤0.031 | 0.5 | 1 |
| NR13553 | ≤0.031 | 0.062 | ≤0.031 | ≤0.031 | 0.5 | 0.25 |
| VPI 10463 | 0.125 | 0.125 | ≤0.031 | ≤0.031 | 0.5 | 0.062 |
| BAA1805* | 0.125 | — | — | — | 1 | 1 |
| C. perfringens MH310 | 1 | 1 | 2 | 2 | 0.5 | 1 |

MIC determined by broth microdilution method; CFM = clofazimine; B746, B4157, B4129 are CFM analogues; VAN = vancomycin; MET = metronidazole.
*Hyper-virulent strain BI/NAP1/027

In addition, MICs of CFM and analogues B746, B4157 and B4129, as well as MICs for VAN and MET, against the various CD strains in BB were determined, as presented in Table 4:

TABLE 4

MIC of CFM and CFM Analogues against CD strains in BB

| Strain: | CFM | B746 | B4157 | B4129 | VAN | MET |
|---|---|---|---|---|---|---|
| HM88 | 0.062 | 0.062 | 0.125 | 0.062 | 0.5 | 1 |
| HM89 | 0.062 | 0.125 | 0.062 | ≤0.031 | 0.5 | 2 |
| HM745 | 0.062 | 0.125 | 0.062 | ≤0.031 | 1 | 2 |
| HM746 | 0.125 | 0.125 | 0.062 | ≤0.031 | 1 | 2 |
| HM747 | 0.062 | 0.125 | ≤0.031 | ≤0.031 | 0.5 | 0.5 |
| NR13427 | 0.125 | 0.125 | 0.062 | 0.062 | 2 | 8 |
| NR13428 | ≤0.031 | 0.125 | ≤0.031 | ≤0.031 | 1 | 0.5 |
| NR13429 | 0.062 | 0.062 | ≤0.031 | ≤0.031 | 0.5 | 4 |
| NR13430 | 0.062 | 0.062 | 0.062 | 0.062 | 1 | 1 |
| NR13431 | 0.125 | 0.125 | 0.062 | 0.062 | 0.5 | 2 |
| NR13432 | 0.062 | 0.125 | ≤0.031 | ≤0.031 | 2 | 2 |

TABLE 4-continued

MIC of CFM and CFM Analogues against CD strains in BB

| Strain: | CFM | B746 | B4157 | B4129 | VAN | MET |
|---|---|---|---|---|---|---|
| NR13433 | 0.062 | 0.062 | ≤0.031 | ≤0.031 | 0.5 | 0.125 |
| NR13434 | ≤0.031 | ≤0.031 | ≤0.031 | ≤0.031 | 0.5 | 0.5 |
| NR13435 | 0.062 | 0.062 | ≤0.031 | ≤0.031 | 0.5 | 0.5 |
| NR13436 | 0.125 | 0.125 | 0.125 | ≤0.031 | 2 | 2 |
| NR13437 | 0.125 | 0.062 | 0.062 | ≤0.031 | 0.5 | 1 |
| NR13438 | 0.25 | 0.5 | ≤0.031 | ≤0.031 | 2 | 2 |
| NR13553 | 0.125 | 0.062 | ≤0.031 | ≤0.031 | 0.5 | 0.5 |
| NR32882 | 0.25 | 0.25 | 0.25 | 0.25 | 0.5 | 0.5 |
| NR32883 | ≤0.031 | 0.062 | ≤0.031 | 0.062 | 0.5 | 1 |
| NR32884 | 0.25 | 0.125 | 0.125 | 0.125 | 1 | 0.5 |
| NR32885 | 0.125 | 0.062 | ≤0.031 | ≤0.031 | 2 | 1 |
| NR32886 | ≤0.031 | 0.062 | ≤0.031 | ≤0.031 | 1 | 1 |
| NR32887 | ≤0.031 | 0.062 | ≤0.031 | ≤0.031 | 1 | 8 |
| NR32888 | 0.25 | 0.5 | ≤0.031 | 0.062 | 0.5 | 1 |
| NR32889 | 0.125 | 0.25 | 0.062 | 0.062 | 2 | 8 |
| NR32890 | 0.062 | ≤0.031 | 0.062 | ≤0.031 | 1 | 1 |
| NR32891 | 0.062 | 0.125 | 0.062 | ≤0.031 | 0.5 | 1 |
| NR32892 | 0.25 | 0.125 | 0.125 | 0.062 | 0.5 | 2 |
| NR32895 | 0.125 | 0.5 | 0.125 | 0.062 | 2 | 4 |
| NR32896 | 0.062 | 0.125 | ≤0.031 | ≤0.031 | 2 | 1 |
| NR32897 | ≤0.031 | 0.062 | ≤0.031 | ≤0.031 | 0.25 | 2 |
| NR32900 | 0.125 | 0.062 | ≤0.031 | ≤0.031 | 0.5 | 1 |
| NR32903 | 0.125 | 0.125 | ≤0.031 | 0.125 | 0.5 | 0.5 |
| NR32904 | 0.125 | 0.125 | 0.062 | 0.125 | 0.5 | 2 |
| VPI 10463 | 0.125 | 0.125 | ≤0.031 | ≤0.031 | 1 | 0.125 |
| BAA1805* | 0.125 | 0.25 | 0.125 | 0.062 | 0.5 | 8 |
| C. perfringens MH310 | 0.5 | 0.5 | 0.5 | 0.25 | 0.25 | 2 |

MIC determined by broth microdilution method;
CFM = clofazimine;
B746, B4157, B4129 = CFM analogues;
VAN = vancomycin;
MET = metronidazole;
*Hyper-virulent strain BI/NAP1/027

As shown in Tables 3 and 4, CFM and CFM analogues exhibited excellent in vitro activity against all CD strains tested. MICs of CFM and CFM analogues B746, B4157 and B4129 in BHI ranged from ≤0.031 to 1.0 μg/ml, while the MICs of VAN and MET ranged from 0.062 to 2.0 μg/ml (Table 3). The MICs of CFM and analogues B746, B4157 and B4129 in BB ranged from ≤0.031 to 0.5 μg/ml, while the MICs of VAN and MET were substantially higher, ranging from 0.125 to 8.0 μg/ml (Table 4).

Antibacterial activity of CFM, analogues B746, B4157 and B4129, VAN and MET against tested CD strains in BB (n=37) is summarized in Table 5 below:

TABLE 5

Antibacterial activity of CFM and CFM Analogue activity against CD

| | CFM | B746 | B4157 | B4129 | VAN | MET |
|---|---|---|---|---|---|---|
| MIC Range (μg/ml) | ≤0.031-0.25 | ≤0.031-0.5 | ≤0.031-0.25 | ≤0.031-0.25 | 0.25-2.0 | 0.125-8 |
| $MIC_{90}$ (μg/ml) | 0.25 | 0.25 | 0.125 | 0.125 | 2 | 4 |
| $MIC_{50}$ (μg/ml) | 0.062 | 0.125 | ≤0.031 | ≤0.031 | 0.5 | 1 |

Based on MIC determined by broth microdilution method in brucella broth (BB);

MIC90 = MIC against 90% of strains;

MIC50 = MIC against 50% of the strains;

n = 37;

CFM is 8-fold more active than VAN and 16-fold more active than MET.

Antibacterial activity exhibited by CFM against CD was about 8-fold greater than VAN and about 16-fold greater than MET (Table 5). Similarly, antibacterial activity exhibited by analogues B746, B4157 and B4129 was substantially greater than that of VAN and MET. Based on $MIC_{90}$ values, B746 exhibited 8-fold greater antibacterial activity as compared to VAN, and 16-fold greater activity as compared to MET. Similarly, B4157 and B4129 exhibited 16-fold greater activity as compared to VAN, and 32-fold greater activity as compared to MET. Thus, CFM and CFM analogues (B746, B4157 and B4129) were determined to be effective antimicrobial agents against CD, and exhibited superior antibacterial activity as compared to both VAN and MET.

Minimum Bactericidal Concentration Screenings:

Minimum bactericidal concentration (MBC) of the test compounds was also determined. 100 µl of the broth from the last three wells or more showing no visible growth (FIG. 4, plate A) was spread on brucella agar/trypticase soy agar plates and incubated in anaerobic chamber at 37° C. The colony forming units (CFUs) were counted after 48 hours. The lowest concentration of the test compound that killed 99.9% of the CD strain was considered to be the MBC. See Jones et al. (1985) *Susceptibility tests: microdilution & macrodilution broth procedures*, in Balows, Hausler, Shadomy (eds.) MANUAL OF CLIN. MICROBIOL., Am. Soc'y Microbiol. Washington, D.C., pp 972-77.

MBC of CFM and VAN was determined against 8 strains of CD, as shown in Table 6:

TABLE 6

| | MBC of CFM and VAN against *C. difficile* | | | | | |
|---|---|---|---|---|---|---|
| | CFM | | | VAN | | |
| CD isolate: | MIC (µg/ml) | MBC (µg/ml) | MBC/ MIC | MIC (µg/ml) | MBC (µg/ml) | MBC/ MIC |
| NR32882 | 0.25 | 0.5 | 2 | 1 | 2 | 2 |
| NR32883 | 0.25 | 0.5 | 2 | 1 | 2 | 2 |
| NR332884 | 0.125 | 0.25 | 2 | 1 | 1 | 1 |
| NR13430 | 0.125 | 0.25 | 2 | 1 | 1 | 1 |
| NR13432 | 0.125 | 0.25 | 2 | 1 | 2 | 2 |
| NR13437 | 0.25 | 0.25 | 1 | 1 | 1 | 1 |
| VPI10463 | 0.125 | 0.25 | 2 | 1 | 4 | 4 |
| BAA1805* | 0.125 | 0.125 | 1 | 0.5 | 2 | 4 |

CFM = clofazimine;
VAN = vancomycin;
note:
vancomycin tolerant colonies were detected at all concentrations in all the strains;
*Hyper-virulent strain BI/NAP1/027

MBC/MIC ratio of CFM ranged from 1-2. MBC/MIC ratio of VAN ranged from 1-4. For the hyper-virulent strain, the ratio for CFM is 1 and for VAN it is 4.

Combination Screening and Synergistic Activity:

CFM is suitable for use with one or more active compounds, such as in combination therapy, and exhibits a synergistic or additive effect with other active compounds. In particular, CFM in combination with MET, VAN and/or FDX exhibits therapeutically effective bactericidal activity, and at a lower dosage as compared to activity of each drug if used alone. Thus, the synergistic effect of such combination enhances activity while beneficially reducing dosage.

Inhibitory activity of CFM in combination with either VAN or MET was determined against 5 strains of CD as shown in Table 7:

TABLE 7

In vitro activity of CFM plus additional antimicrobial agent(s) against CD

| Strain: | Test | Drug combination | MIC (µg/ml) alone | MIC (µg/ml) combination | FIC | ΣFIC |
|---|---|---|---|---|---|---|
| VPI 10463 | 1 | CFM | 0.25 | 0.031 | 0.124 | 0.374 |
| | | VAN | 2 | 0.5 | 0.25 | |
| | 2 | CFM | 0.125 | 0.0039 | 0.0312 | 0.281 |
| | | VAN | 2 | 0.5 | 0.25 | |
| | 3 | CFM | 0.125 | 0.062 | 0.5 | 1 |
| | | MET | 0.125 | 0.062 | 0.5 | |
| | 4 | CFM | 0.125 | 0.062 | 0.5 | 1 |
| | | MET | 0.125 | 0.062 | 0.5 | |
| NR32889 | 5 | CFM | 0.125 | 0.125 | 1 | 2 |
| | | VAN | 2 | 2 | 1 | |
| NR32890 | 6 | CFM | 0.125 | 0.031 | 0.25 | 0.75 |
| | | VAN | 1 | 0.5 | 0.5 | |
| NR32885 | 7 | CFM | 0.125 | 0.062 | 0.5 | 1 |
| | | VAN | 1 | 0.5 | 0.5 | |
| | 8 | CFM | 0.125 | 0.031 | 0.25 | 0.375 |
| | | MET | 2 | 0.25 | 0.125 | |
| | 9 | CFM | 0.25 | 0.062 | 0.25 | 0.5 |
| | | VAN | 1 | 0.25 | 0.25 | |
| | 10 | CFM | 0.125 | 0.0039 | 0.031 | 0.281 |
| | | MET | 1 | 0.25 | 0.25 | |
| | 11 | CFM | 0.25 | 0.062 | 0.25 | 0.5 |
| | | VAN | 1 | 0.25 | 0.25 | |
| | 12 | CFM | 0.25 | 0.0078 | 0.031 | 0.281 |
| | | MET | 1 | 0.25 | 0.25 | |
| BAA1805* | 13 | CFM | 0.25 | 0.062 | 0.25 | 0.312 |
| | | VAN | 0.5 | 0.031 | 0.062 | |
| | 14 | CFM | 0.25 | 0.0039 | 0.015 | 0.031 |
| | | MET | 16 | 0.25 | 0.015 | |
| | 15 | CFM | 0.25 | 0.015 | 0.06 | 0.185 |
| | | MET | 32 | 4 | 0.125 | |
| | 16 | CFM | 0.25 | 0.062 | 0.25 | 0.5 |
| | | VAN | 0.5 | 0.125 | 0.25 | |
| | 17 | CFM | 0.25 | 0.0078 | 0.031 | 0.156 |
| | | MET | 32 | 4 | 0.125 | |
| NR32888 | 18 | CFM | 0.25 | 0.125 | 0.5 | 1 |
| | | VAN | 0.5 | 0.25 | 0.5 | |
| | 19 | CFM | 0.25 | 0.015 | 0.062 | 0.125 |
| | | MET | 2 | 0.125 | 0.062 | |
| | 20 | CFM | 0.25 | 0.062 | 0.25 | 0.75 |
| | | VAN | 0.5 | 0.25 | 0.5 | |
| | 21 | CFM | 0.25 | 0.0078 | 0.031 | 0.28 |
| | | MET | 2 | 0.5 | 0.25 | |

ΣFIC ≤ 0.5: indicates synergistic or beneficial effect of drug combination (as compared to effect of drug if used alone);
ΣFIC ≥ 4.0: indicates antagonistic or detrimental effect of drug combination (as compared to effect or activity of each drug if used alone, thus interfering with effectiveness of each drug alone);
ΣFIC > 0.5 but < 4.0: indicates additive effect of drug combination (thus indicating drug may act as substitute for the other).
*Hyper-virulent strain BI/NAP1/027

As shown in Table 7, a fractional inhibitory concentration (FIC) is provided for each drug alone, as well as the total or sum factional inhibitory concentration (ΣFIC) for each drug combination. As shown by the data, all drug combinations exhibited either a synergistic effect (in most cases) or an additive effect (in two of the tested cases), as compared to the activity of each drug alone.

Of note, where clinically virulent strain NAP1/B1/027 MET is becoming ineffective, and where MET alone is virtually ineffective against CD strain BI/NAP1/027 in BB culture (MIC 32 µg/ml), when treated in combination with 0.008 µg of CFM, MIC for MET is reduced to 4 µg/ml for this virulent CD strain. A similar synergistic effect with FDX is likewise provided against virulent CD strains. Thus, the data demonstrate a substantial reduction in effective dosage requirements of each antibiotic if used alone. Moreover, such combination therapy substantially reduces the potential emergence of resistant CD strains.

CFM and CFM Analogue Activity Against Other Bacterial Species:

In vitro activity of CFM and CFM analogues (B746, B4157 and B4129) was determined against a panel of other bacteria representing a portion of normal gut flora, including strains of *Escherichia coli* (Gram-negative), *Enterococcus faecalis, Enterococcus faecium* (Gram-positive), *Staphylococcus aureus* (Gram-positive), *Bacteroides* spp. (Gram-negative anaerobic bacteria that are predominant representative normal bacterial flora in the human colon), *Fusobacteria* spp. (Gram-negative, anaerobic, non-spore forming bacteria), *Bifidobacterium* spp. (Gram-positive, non-spore forming, anaerobic, branched bacilli), Lactobacilli (Gram-positive, facultative anaerobic, non-spore forming bacteria, also found in urogenital canal, in acidic environment) and Lachnospiraceae and related organisms (Gram-positive, anaerobic bacteria).

As shown in Tables 8-15 below, except for Lachnospiraceae, CFM was not effective in inhibiting growth of these other tested bacteria at concentrations demonstrated to be effective against CD. The tested bacterial species, when present in certain proportions in the gut, are known to resist colonization of CD. See Schubert et al. (2015) *Antibiotic-Induced Alterations of the Murine Gut Microbiota & Subsequent Effects on Colonization Resistance against Clostridium difficile*, Mbio.asm.org 6(4):e000974-15, pp. 1-10). As such, they are beneficially maintained in accordance with the disclosed methods and compositions of the present invention.

MICs for CFM, CFM analogues (B746, B4157 and B4129), VAN, MET, CIP, AMP and AMK against *Escherichia coli* strains are presented in Table 8:

TABLE 8

Antibacterial activity of CFM and CFM Analogues against *Escherichia coli* strains

| Strain: | MIC (µg/ml) | | | | | | | | |
| --- | --- | --- | --- | --- | --- | --- | --- | --- | --- |
| | CFM | B746 | B4157 | B4129 | VAN | MET | CIP | AMP | AMK |
| NR 6 | >32 | >32 | >32 | >32 | >32 | >32 | ≤0.031 | 2 | 4 |
| NR 8 | >32 | >32 | >32 | >32 | >32 | >32 | ≤0.031 | 4 | 4 |
| NR 96 | >32 | >32 | >32 | >32 | >32 | >32 | ≤0.031 | 4 | 8 |
| NR 104 | >32 | >32 | >32 | >32 | >32 | >32 | ≤0.031 | 4 | 2 |
| NR 17626 | >32 | >32 | >32 | >32 | >32 | >32 | ≤0.031 | 4 | 16 |
| NR 17627 | >32 | >32 | >32 | >32 | >32 | >32 | ≤0.031 | 4 | 8 |
| NR 17633 | >32 | >32 | >32 | >32 | >32 | >32 | ≤0.031 | 4 | 8 |
| NR 17647 | >32 | >32 | >32 | >32 | >32 | >32 | ≤0.031 | 4 | 2 |
| NR 17650 | >32 | >32 | >32 | >32 | >32 | >32 | ≤0.031 | 4 | 8 |
| NR 17661 | >32 | >32 | >32 | >32 | >32 | >32 | >32 | >32 | 2 |

MIC determined by microdilution method in Mueller-Hinton broth;
CFM = clofazimine;
B746, B4157, B4129 = CFM analogues;
VAN = vancomycin;
MET = metronidazole;
CIP = ciprofloxacin (Fluoroquinolones);
AMP = ampicillin (Beta-Lactam);
AMK = amikacin (aminoglycoside)

MICs for CFM, CFM Analogues (B746, B4157 and B4129), VAN, MET, CIP, AMP and AMK against *Enterococci faecalis* and *Enterococci faecium* strains are presented in Table 9. As shown, the activity demonstrated by CFM and B746 against *Enterococci faecium* is far superior to that demonstrated by conventional drugs tested (e.g., MET, VAN and FDX). Thus, CFM and CFM analogues (and in particular B746) are suitable and advantageous candidates for effectively treating CDAD, while also minimizing the risk of emergence of resistant strains (e.g., VRE). Indeed, despite its long-term use in the treatment of leprosy and *Mycobacterium tuberculosis* (MTB), CFM has shown negligible incidences of emergence of resistant strains.

TABLE 9

Antibacterial activity of CFM and CFM Analogue activity against *Enterococcus faecalis* and *Enterococci faecium* strains

| Species & Strain: | MIC (µg/ml) | | | | | | | | |
| --- | --- | --- | --- | --- | --- | --- | --- | --- | --- |
| | CFM | B746 | B4157 | B4129 | VAN | MET | CIP | AMP | AMK |
| *E. faecalis* NR 31884 | 32 | 4 | >32 | >32 | 2 | >32 | 1 | 4 | >32 |
| *E. faecalis* NR 31885 | 32 | 4 | >32 | >32 | 2 | >32 | 0.5 | 4 | >32 |

TABLE 9-continued

Antibacterial activity of CFM and CFM Analogue activity against *Enterococcus faecalis* and *Enterococci faecium* strains

| Species & Strain: | MIC (µg/ml) | | | | | | | | |
|---|---|---|---|---|---|---|---|---|---|
| | CFM | B746 | B4157 | B4129 | VAN | MET | CIP | AMP | AMK |
| *E. faecalis* NR 31886 | 32 | 8 | >32 | >32 | 1 | >32 | 0.5 | 4 | >32 |
| *E. faecalis* NR 31887 | 16 | 4 | >32 | >32 | 1 | >32 | 0.5 | 0.5 | >32 |
| *E. faecalis* NR 31888 | 32 | 8 | >32 | >32 | 2 | >32 | 1 | 4 | >32 |
| *E. faecium* NR 31903 | 4 | 2 | >32 | >32 | >32 | >32 | >32 | >32 | >32 |
| *E. faecium* NR 31909 | 2 | 2 | >32 | >32 | >32 | >32 | >32 | >32 | >32 |
| *E. faecium* NR 31912 | 2 | 2 | >32 | >32 | >32 | >32 | >32 | >32 | >32 |
| *E. faecium* NR 31915 | 16 | 2 | >32 | >32 | >32 | >32 | 4 | 2 | >32 |
| *E. faecium* NR 31916 | 8 | 2 | >32 | >32 | >32 | >32 | 1 | >32 | >32 |

MIC determined by microdilution method in Mueller-Hinton broth;
CFM = clofazimine;
B746, B4157, B4129 = CFM analogues;
VAN = vancomycin;
MET = metronidazole;
CIP = ciprofloxacin;
AMP = ampicillin;
AMK = amikacin MICs for CFM, analogues B746, B4157 and B4129, VAN, MET, CIP, AMP and AMK against *Staphylococcus aureus* strains are presented in Table 10:

TABLE 10

Antibacterial activity of CFM and CFM Analogues against *Staphylococcus aureus* strains

| Strain: | MIC (µg/ml) | | | | | | | | |
|---|---|---|---|---|---|---|---|---|---|
| | CFM | B746 | B4157 | B4129 | VAN | MET | CIP | AMP | AMK |
| NR 10129 | 16 | 4 | 32 | 32 | 1 | >32 | 2 | >32 | 2 |
| NR 10186 | 2 | 2 | 16 | >32 | 1 | >32 | 32 | >32 | 32 |
| NR 10187 | >32 | 4 | >32 | >32 | 2 | >32 | >32 | 8 | >32 |
| NR 10188 | 8 | 4 | 32 | >32 | 1 | >32 | >32 | 16 | >32 |
| NR 10189 | 8 | 4 | >32 | >32 | 2 | >32 | 1 | 32 | 4 |
| NR 10191 | 4 | 4 | 32 | >32 | 1 | >32 | >32 | >32 | 32 |
| NR 10192 | 8 | 4 | >32 | >32 | 1 | >32 | >32 | 32 | >32 |
| NR 10193 | 4 | 4 | 32 | >32 | 2 | >32 | >32 | >32 | >32 |
| NR 10194 | 4 | 4 | 16 | 32 | 1 | >32 | 0.5 | 2 | 32 |
| NR 10198 | 16 | 16 | >32 | >32 | 2 | >32 | >32 | >32 | >32 |

MIC determined by microdilution method in Mueller-Hinton broth;
CFM = clofazimine;
B746, B4157, B4129 = CFM analogues;
VAN = vancomycin;
MET = metronidazole;
CIP = ciprofloxacin;
AMP = ampicillin;
AMK = amikacin MICs for CFM, analogues B746, B4157 and B4129, AZQ, VAN and MET against *Bacteroides* strains are presented in Table 11:

TABLE 11

Antibacterial activity of CFM and CFM Analogues against *Bacteroides* Strains

| | | MIC (µg/ml) | | | | | | |
|---|---|---|---|---|---|---|---|---|
| Species: | Strain: | CFM | B746 | B4157 | B4129 | AZQ | VAN | MET |
| B. sp. | HM18 | 4 | 1 | 2 | 16 | 2 | >32 | 4 |
| B. sp. | HM19 | 1 | 2 | 0.5 | 0.5 | 4 | >32 | 1 |
| B. sp. | HM20 | 2 | 1 | 2 | 2 | 2 | 16 | 0.25 |
| B. sp. | HM22 | 2 | 1 | 1 | 2 | 2 | 32 | 0.5 |
| B. sp. | HM23 | 2 | 2 | 2 | 16 | 2 | 8 | 0.25 |
| B. sp. | HM27 | 1 | 1 | 0.5 | 1 | 1 | 16 | 0.5 |
| B. sp.. | HM28 | 2 | 2 | 2 | 2 | 2 | >32 | 2 |
| B. sp. | HM58 | 1 | 1 | 1 | 2 | 4 | 32 | 2 |
| B. eggerthii | HM210 | 2 | 2 | 1 | 2 | 2 | 32 | 0.5 |
| B. ovatus | HM222 | 0.25 | 0.25 | 0.25 | 0.25 | 1 | 4 | 0.5 |
| B. fragilis | HM709 | 4 | 4 | 2 | 2 | 2 | 8 | 1 |
| B. fragilis | HM710 | 2 | 2 | 2 | 2 | 2 | 8 | 0.5 |
| B. fragilis | HM714 | 2 | 4 | 2 | 4 | 2 | 16 | 1 |
| B. caccae | HM728 | 1 | 1 | 2 | 2 | 2 | 32 | 0.25 |
| B. stercoris | HM1036 | 0.5 | 1 | 0.5 | 0.25 | 2 | 16 | 0.25 |

MIC determined by microdilution method in *Brucella* broth;
CFM = clofazimine;
B746, B4157, B4129 = CFM analogues;
AZQ = azaquinone;
VAN = vancomycin;
MET = metronidazole As shown by data presented in Tables 8, 9 and 10 above, CFM and CFM analogues B746, B4157 and B4129 were relatively inactive against *E. coli*, and relatively inactive to only modestly active against other Gram-positive bacteria with higher MICs. All tested compounds were less active than VAN against *Enterococcus* and *S. aureus* strains tested. As shown in Table 11, CFM and CFM analogues also exhibited good in vitro activity against *Bacteroides* strains (e.g., wherein antibacterial activity was significantly superior to VAN and comparable to MET).

As shown above, CFM kills *Bacteroides* spp. in in-vitro assays. Crohn's disease patients have a preponderance of these Gram-negative anaerobic bacteria in their guts as compared to normal population. See Bibiloni et al. (2006) *The bacteriology of biopsies differs between newly diagnosed, untreated, Crohn's disease & ulcerative colitis patients*, J. Med. Microbiol. 55:1141-49. As demonstrated herein, CFM's significant effect on the disease is by inhibiting the growth of these *Bacteroides* in the gut of patients with Crohn's disease, when used alone (see Afdhal et al. (1991) *Controlled trial of anti-microbial therapy in Crohn's disease: clofazimine versus placebo*, Dig. Dis. Sci. 36:449-53) or when used in combination therapies (Prantera et al. (1994) *Antimycobacterial therapy in Crohn's Disease: results of a controlled double blind trial with a multiple antibiotic regimen*, Am. J. Gastroentrol. 89:513-18; Selby et al. (2007) *Two year combination antibiotic therapy with clarithromycin, rifabutin, and clofazimine for Crohn's disease*, Gastroenterol. 132:2313-19).

CFM and CFM analogues show limited or no in vitro activity against *Fusobacterium* spp., as shown in Table 12 below. Fusobacteria are Gram-negative, anaerobic, non-spore forming bacteria that are part of the normal flora of the gastrointestinal tract. Moderate activity is seen for HM-993 strain, though such activity is at least 8-fold less than that observed against a majority of CD strains. VAN was completely inactive against these strains (MIC>32 µg/ml). However, MET displayed excellent activity with MIC ranging from ≤0.031-0.5 µg/ml.

TABLE 12

Antibacterial activity of CFM and CFM Analogues against *Fusobacterium*

| | | MIC (µg/ml) | | | | | | |
|---|---|---|---|---|---|---|---|---|
| Species: | Strain: | CFM | B746 | B4157 | B4129 | VAN | MET | CIP |
| F. sp. | HM 42 | >32 | >32 | >32 | >32 | >32 | 0.125 | — |
| F. sp. | HM 57 | >32 | >32 | >32 | >32 | >32 | 0.5 | — |
| F. sp. | HM-556 | 16 | 8 | >32 | >32 | >32 | 0.125 | 2 |
| F. sp. | HM-758 | >32 | >32 | >32 | >32 | >32 | 0.125 | 1 |
| F. sp. | HM-871 | 32 | 8 | >32 | >32 | >32 | 0.125 | 2 |
| F. sp.. | HM-874 | >32 | 16 | >32 | >32 | >32 | 0.125 | 2 |
| F. sp. | HM-875 | 32 | 8 | >32 | >32 | >32 | 0.125 | 1 |
| F. nucleatum | HM-75 | >32 | 16 | >32 | >32 | >32 | 0.062 | 1 |
| F. nucleatum | HM-260 | >32 | >32 | >32 | >32 | >32 | 0.125 | 1 |
| F. nucleatum | HM-992 | >32 | 16 | >32 | >32 | >32 | 0.125 | 1 |
| F. nucleatum | HM-993 | 2 | 2 | 4 | 8 | >32 | ≤0.031 | 1 |
| F. nucleatum | HM-994 | 32 | 8 | >32 | >32 | >32 | 0.125 | 1 |
| F. nucleatum | HM-995 | >32 | 16 | >32 | >32 | >32 | 0.125 | 2 |

TABLE 12-continued

Antibacterial activity of CFM and CFM Analogues against *Fusobacterium*

| Species: | Strain: | MIC (μg/ml) | | | | | | |
|---|---|---|---|---|---|---|---|---|
| | | CFM | B746 | B4157 | B4129 | VAN | MET | CIP |
| *F. nucleatum* | HM-996 | 32 | 32 | >32 | >32 | >32 | 0.5 | 2 |
| *F. nucleatum* | HM-997 | >32 | 16 | >32 | >32 | >32 | 0.25 | 1 |

MIC determined by microdilution method in *Brucella* broth;
CFM = clofazimine;
B746, B4157, B4129 are CFM analogues;
VAN = vancomycin;
MET = metronidazole;
CIP = ciprofloxacin CFM showed modest or no activity against *Bifidobacterium* spp., as shown in Table 13 below. *Bifidobacterium* spp. are Gram-positive, non-spore forming, anaerobic, branched bacilli that are also part of the normal flora of the gastrointestinal tract. CFM analogues showed modest in vitro activity against nine of the ten strains tested (MIC 0.5-2 μg/ml) and no activity against one strain tested. Tested CFM analogues were found to be less active than CFM (Table 13). Except for one resistant strain, VAN displayed high activity against these bacteria, with MIC ranging from 0.25 to 1 μg/ml. MET activity was variable, with four of the ten strains susceptible.

Overall, the data show that strains of *Bifidobacterium longum* species tested are more susceptible to this group of antibiotics than other species, suggesting the utilization of individualized patient treatments. For example, a patient harboring strain HM-845 of *Bifidobacterium longum* may be best served by using CFM analog B4157 compared to the use of other antibiotics for CD treatment.

In vitro activity of CFM and its analogues against *Lactobacillus* spp. was variable, as shown in Table 14. Lactobacilli are Gram-positive, facultative anaerobic, non-spore forming bacteria normally live in gastrointestinal and urogenital tracts, in acidic environment, preventing colonization of pathogenic organisms. Of the ten species strains tested, six were resistant to the CFM analogues, and four were moderately susceptible. However, MIC values against these four strains were still 4- to 8-fold higher than those required to inhibit CD by CFM. Similarly, in vitro activity of VAN was variable, with six strains susceptible and four resistant. MET was essentially inactive against all strains tested.

TABLE 13

Antibacterial activity of CFM and CFM Analogues against *Bifidobacterium* strains

| Species: | Strain: | MIC (μg/ml) | | | | | | |
|---|---|---|---|---|---|---|---|---|
| | | CFM | B746 | B4157 | B4129 | VAN | MET | CIP |
| *B.* sp. | HM-30 | 0.5 | 1 | 8 | 4 | 0.5 | >32 | >32 |
| *B. breve* | HM-411 | 2 | 4 | 16 | >32 | 0.5 | >32 | 4 |
| *B. breve* | HM-412 | 2 | 4 | 4 | 0.25 | 0.5 | >32 | 4 |
| *B. adolescentis* | HM-633 | 1 | 2 | 16 | >32 | 0.5 | >32 | 8 |
| *B. longum* | HM-845 | 1 | 2 | 32 | ≤0.031 | 0.5 | 2 | 4 |
| *B. longum* | HM-846 | 2 | 2 | 8 | 0.25 | 0.5 | 2 | 4 |
| *B. longum* | HM-847 | 1 | 2 | 1 | 2 | 0.5 | 1 | 8 |
| *B. breve* | HM-856 | 4 | 32 | >32 | >32 | 1 | >32 | >32 |
| *B.* sp. | HM-868 | 2 | 2 | 32 | >32 | 0.25 | 16 | 0.5 |
| *B. breve* | HM-1120 | >32 | >32 | >32 | >32 | 8 | 0.5 | >32 |

MIC determined by microdilution method in BHI broth;
CFM = clofazimine;
B746, B4157, B4129 are CFM analogues;
VAN = vancomycin;
MET = metronidazole;
CIP = ciprofloxacin

TABLE 14

Antibacterial activity of CFM and CFM Analogues against *Lactobacillus* strains

| Species: | Strain: | MIC (µg/ml) | | | | | | |
|---|---|---|---|---|---|---|---|---|
| | | CFM | B746 | B4157 | B4129 | VAN | MET | CIP |
| *L. rhamnosus* | HM-106 | >32 | >32 | >32 | >32 | >32 | >32 | 2 |
| *L.* sp. | HM-228 | 1 | 4 | ≤0.031 | 1 | 1 | >32 | 4 |
| *L. gasseri* | HM-104 | >32 | 16 | >32 | >32 | 1 | >32 | >32 |
| *L. jensenii* | HM-105 | >32 | >32 | >32 | >32 | 1 | >32 | 32 |
| *L. crispatus* | HM-637 | 4 | 8 | 2 | 16 | 0.5 | >32 | >32 |
| *L. iners* | HM-126 | 2 | 4 | 2 | 1 | 1 | >32 | 2 |
| *L. vaginalis* | HM-405 | 2 | 4 | 2 | 2 | >32 | >32 | >32 |
| *L.* sp. | HM-478 | >32 | 16 | >32 | >32 | >32 | >32 | >32 |
| *L. jhonsonii* | HM-643 | >32 | 32 | >32 | >32 | 2 | >32 | >32 |
| *L. reuteri* | HM-102 | >32 | 32 | >32 | >32 | >32 | >32 | >32 |

MIC determined by broth microdilution method in BHI with 0.02% Tween 80, pH 6.0;
CFM = clofazimine;
B746, B4157 & B4129 are CFM analogs;
VAN = vancomycin;
MET = metronidazole;
CIP = ciprofloxacin In vitro activity of CFM and its analogues against Lachnospiraceae spp. is presented in Table 15. Lachnospiraceae and related organisms are Gram-positive, anaerobic bacteria that are part of normal flora of the gut. Most of the members of this family were found to be susceptible to CFM, CFM analogues, VAN and MET. Their susceptibility of ciprofloxacin was variable.

TABLE 15

Antibacterial activity of CFM and CFM Analogues against *Lachnospiraceae* and related bacterial strains

| Species: | Strain: | MIC (µg/ml) | | | | | | |
|---|---|---|---|---|---|---|---|---|
| | | CFM | B746 | B4157 | B4129 | VAN | MET | CIP |
| *Lachnospiraceae* sp. | HM-150 | 0.25 | 0.5 | 0.25 | 0.125 | 1 | 0.25 | 16 |
| *Lachnospiraceae* sp. | HM-153 | 0.125 | 0.5 | 0.25 | 0.125 | 4 | 0.062 | 4 |
| *Lachnospiraceae* sp. | HM-480 | 0.062 | 0.125 | ≤0.031 | 0.062 | 0.25 | 0.5 | 16 |
| *Lachnospiraceae* sp. | HM-157 | 0.125 | 0.5 | 0.5 | 0.25 | 0.5 | 0.25 | >32 |
| *Lachnospiraceae* sp. | HM-161 | 0.25 | 0.25 | 0.125 | 0.125 | 0.5 | 0.125 | 32 |
| *Lachnospiraceae* sp. | HM-7 | ≤0.031 | ≤0.031 | ≤0.031 | ≤0.031 | 0.125 | 0.25 | 8 |
| *Lachnospiraceae* sp. | HM-154 | 0.5 | 0.5 | 0.5 | 0.125 | 0.5 | 0.125 | 16 |
| *Lachnospiraceae* sp. | HM-558 | 0.062 | 0.125 | 0.062 | 0.125 | 0.25 | 0.5 | 16 |
| *Lachnospiraceae* sp. | HM-768 | ≤0.031 | ≤0.031 | ≤0.031 | ≤0.031 | 0.125 | 0.5 | 8 |
| *Lachnospiraceae* sp. | HM-868 | 2 | 2 | 32 | >32 | 0.25 | 16 | 0.5 |
| *Clostridiales bacterium* | HM-182 | 0.25 | 1 | 0.5 | 0.125 | 0.25 | ≤0.031 | 8 |
| *Eubacterium* sp. | HM-178 | 0.125 | 0.5 | 1 | 0.125 | 2 | 1 | 0.5 |
| *Peptostreptococcaceae* sp. | HM-766 | 1 | 1 | 0.5 | 0.5 | 0.5 | 0.5 | 0.25 |
| *Clostridiales bacterium* | HM-84 | ≤0.031 | 0.062 | ≤0.031 | ≤0.031 | 0.5 | 0.25 | 16 |

MIC determined by broth microdilution method in *brucella* broth;
CFM = clofazimine;
B746, B4157, and B4129 are CFM analogs;
VAN = vancomycin;
MET = metronidazole;
CIP = ciprofloxacin.

AZQ Activity Against CD Strains:

AZQ exhibited excellent antibacterial activity against CD strains, with very narrow MIC range (0.25-1 µg/ml). AZQ activity was comparable to VAN and superior to MET. MIC data for AZQ, VAN and MET are presented in Table 16:

TABLE 16

MIC of AZQ against CD strains

| Strain: | MIC (µg/ml) | | |
|---|---|---|---|
| | AZQ | VAN | MET |
| VPI 10463 | 0.5 | 1 | 0.125 |
| HM88 | 1 | 0.5 | 1 |
| HM89 | 1 | 0.5 | 2 |
| HM745 | 1 | 1 | 2 |
| HM746 | 1 | 1 | 2 |
| HM747 | 1 | 0.5 | 0.5 |
| NR13427 | 1 | 2 | 8 |
| NR13428 | 1 | 1 | 0.5 |
| NR13429 | 1 | 0.5 | 4 |
| NR13430 | 0.5 | 1 | 1 |
| NR13431 | 1 | 0.5 | 2 |
| NR13432 | 1 | 2 | 2 |
| NR13433 | 1 | 0.5 | 0.125 |
| NR13434 | 0.25 | 0.5 | 0.5 |
| NR13435 | 1 | 0.5 | 0.5 |
| NR13436 | 1 | 2 | 2 |
| NR13437 | 1 | 0.5 | 1 |
| NR13438 | 1 | 2 | 2 |
| NR13553 | 1 | 0.5 | 0.5 |
| NR32882 | 1 | 0.5 | 0.5 |
| NR32883 | 0.5 | 0.5 | 1 |
| NR32884 | 1 | 1 | 0.5 |
| NR32885 | 1 | 2 | 1 |
| NR32886 | 1 | 1 | 1 |
| NR32887 | 1 | 1 | 8 |
| NR32888 | 1 | 0.5 | 1 |
| NR32889 | 1 | 2 | 8 |
| NR32890 | 0.5 | 1 | 1 |
| NR32891 | 1 | 0.5 | 1 |
| NR32892 | 1 | 0.5 | 2 |
| NR32895 | 1 | 2 | 4 |
| NR32896 | 1 | 2 | 1 |
| NR32897 | 1 | 0.25 | 2 |
| NR32900 | 1 | 0.5 | 1 |
| NR32903 | 1 | 0.5 | 0.5 |
| NR32904 | 1 | 0.5 | 2 |

MIC determined by broth microdilution method in brucella broth;
AZQ = azaquinone;
VAN = vancomycin;
MET = metronidazole;
$MIC_{90}$ of AZQ = 1 µg/ml,
VAN = 2 µg/ml and
MET = 4 µg/ml.

AZQ Activity Against Other Bacterial Strains:

Antibacterial activity of AZQ was also tested against other bacteria representing normal gut floral. AZQ exhibited no activity against Gram-negative bacteria (*E. coli*) and relatively low levels of activity against other Gram-positive bacteria. MIC data for AZQ, VAN, CIP, AMP and AMK against *E. coli, Staphylococcus aureus, Enterococcus faecalis*, and *Enterococcus faecium* are presented in Table 17. AZQ exhibited good in vitro activity against *Bacteroides* spp. (see Table 11), wherein antibacterial activity was significantly superior to VAN and comparable to MET).

TABLE 17

Activity against other facultative anaerobic bacteria

| Organism: | Strain: | MIC (µg/ml) | | | | |
|---|---|---|---|---|---|---|
| | | AZQ | VAN | CIP | AMP | AMK |
| E. coli | NR 6 | >32 | >32 | ≤0.031 | 2 | 4 |
| | NR 8 | >32 | >32 | ≤0.031 | 4 | 4 |
| | NR 96 | >32 | >32 | ≤0.031 | 4 | 8 |
| | NR 104 | >32 | >32 | ≤0.031 | 4 | 2 |
| | NR 17626 | >32 | >32 | ≤0.031 | 4 | 16 |
| | NR 17627 | >32 | >32 | ≤0.031 | 4 | 8 |
| | NR 17633 | >32 | >32 | ≤0.031 | 4 | 8 |
| | NR 17647 | >32 | >32 | ≤0.031 | 4 | 2 |
| | NR 17650 | >32 | >32 | ≤0.031 | 4 | 8 |
| | NR 17661 | >32 | >32 | >32 | >32 | 2 |
| S. aureus | NR 10129 | 32 | 1 | 2 | >32 | 2 |
| | NR 10186 | 16 | 1 | 32 | >32 | 32 |
| | NR 10187 | >32 | 2 | >32 | 8 | >32 |
| | NR 10188 | 32 | 1 | >32 | 16 | >32 |
| | NR 10189 | 16 | 2 | 1 | 32 | 4 |
| | NR 10191 | 8 | 1 | >32 | >32 | 32 |
| | NR 10192 | 32 | 1 | >32 | 32 | >32 |
| | NR 10193 | 16 | 2 | >32 | >32 | >32 |
| | NR 10194 | 16 | 1 | 0.5 | 2 | 32 |
| | NR 10198 | 16 | 2 | >32 | >32 | >32 |
| E. faecalis | NR 31884 | 32 | 2 | 1 | 4 | >32 |
| | NR 31885 | 32 | 2 | 0.5 | 4 | >32 |
| | NR 31886 | 32 | 1 | 0.5 | 4 | >32 |
| | NR 31887 | 16 | 1 | 0.5 | 0.5 | >32 |
| | NR 31888 | 32 | 2 | 1 | 4 | >32 |
| E. faecium | NR 31903 | >32 | >32 | >32 | >32 | >32 |
| | NR 31909 | 32 | >32 | >32 | >32 | >32 |
| | NR 31912 | 32 | >32 | >32 | >32 | >32 |
| | NR 31915 | >32 | >32 | 4 | 2 | >32 |
| | NR 31916 | 16 | >32 | 1 | >32 | >32 |

MIC determined by broth microdilution method in Mueller-Hinton broth.
AZQ = azaquinone;
VAN = vancomycin;
CIP = ciprofloxacin;
AMP = ampicillin;
AMK = amikacin.

Animal Model Testing and Observations:

For the treatment of CDAD, CFM is retained in the gut in a therapeutically sufficient concentration and sufficient period of time for clearing CDI. Animal model tests (e.g., Syrian Golden Hamster model) were conducted utilizing three doses of CFM in aqueous suspension of carboxy methyl cellulose (CMC), administered orally to the animals (10, 20 and 40 mg/kg body weight/day, once a day) for 5 days.

Efficacy of CMC formulation with Lamprene® at doses 10 mg/kg and 20 mg/kg twice a day were compared. Efficacy of a combination of Lamprene® at 10 mg/kg+VAN at 5 mg/kg (administered orally twice a day) was also compared with VAN at 5 mg/kg alone and with Lamprene® at 10 mg/kg alone (administered orally twice a day). Data from these experiments conformed to results demonstrated by in vitro testing.

At lower doses of CFM of 10 mg/kg/day, 50% protection was observed on animal survival by day 9 after infection was achieved. In contrast, all ten animals in the control groups died by day 10. Beyond 10 days, protection diminished for some animals. 30% protection was observed for CFM dosage of 10 mg/kg during 28 days of observation. However, higher dosages of 20 and 40 mg/kg did not increase the protection.

As expected, treatment of animals with CFM in aqueous suspension of CMC at 10 mg/kg/once a day was demonstrated to be more promising (30% survival for 27 days) compared to survival of animals treated with Lamprene®, which is intended for systemic absorption, at 10 mg/kg or 20 mg/kg twice a day (0% survival by 7 days). In addition, animal groups treated with a combination of Lamprene® (lower dose) with a low dose of VAN fared much better (40% survival) compared to groups treated with each drug alone at the same dosage (0% survival by day 7 for CFM and 0% survival by day 14 for VAN).

Thus, dosage used for some experiments was too high. According to dose translation calculations from humans to animals, 20 mg/kg for hamsters is the upper tolerable limit (see Reagan-Shaw et al. (2007) *Dose translation from animal to human studies revisited*, FASEB J. 22:659-61), though such limit may be too high for animals challenged with CD. Thus, a dosage of 5-7 mg/kg is more suitable.

CFM Solubility:

CFM is poorly soluble in water. Thus, CFM is typically administered in an oil-based formulation, wherein the drug is suspended in a mixture of oils and emulsifying agents in a gel-capsule. In the treatment of leprosy and multi-drug resistant TB (MDR-TB), such formulation is also typically optimized for better systemic absorption.

However, the success treatment of CD requires that the drug stay in the gut for a much longer period as compared to treatments for leprosy and MDR-TB. Despite excellent in vitro activity against CD, relatively low therapeutic efficacy in hamster models was seen in preliminary studies due to poor CFM solubility and availability in the presence of fecal matter. Several formulations were therefore developed for effective in vivo dosing for CD therapies (Table 18), which exhibit improved solubility and efficacy in the gut in the presence of fecal matter.

TABLE 19

In vitro activity of CFM-formulations

| Drug/formulation | MIC (µg/ml) | MBC (µg/ml) |
| --- | --- | --- |
| CFM-DMSO | 0.25 | 0.25 |
| CFM-PEG | 0.125 | 0.125 |
| CFM-CrEL | 0.125 | 0.125 |
| CFM-Tween | 0.125 | 0.125 |
| VAN | 0.5 | 2.0 |
| MET | 0.25 | 0.25 |

Organism and strain: CD strain VPI 10463;
Medium used: BHI;
CFM = clofazimine;
DMSO = dimethyl sulfoxide;
PEG = polyethylene glycol;
CrEL = cremophor EL;
Tween = Tween 80;
VAN = vancomycin;
MET = metronidazole.

Drugs may bind to organic matter in the body and lose their activity. To be effective, the compound should display antibacterial activity against CD in the presence of fecal matter. To determine the effect of soluble fecal matter on in vitro activity of CFM, normal healthy human feces was suspended in BHI broth at 20% w/v, mixed well and filter

TABLE 18

CFM formulations suitable for in vivo dosing

| Agent | Form and strength | Solubility | Stability | Comments |
| --- | --- | --- | --- | --- |
| Polyethylene glycol (PEG-300, PEG-400) | Liquid, 100% | 5 mg/ml | Stable undiluted, the drug opalescent following dilution in water or medium; precipitates faster in saline/PBS | Works well in in vitro studies; however, because the drug precipitates upon dilution, it may not be useful for in vivo studies. |
| Cremophor-EL | Liquid, 100% | 8 mg/ml 10 mg/ml if kept for long time (3-5 days) | Stable, and remains stable following dilution in water/ medium/saline/PBS | Most stable formulation and remains clear upon dilution and most suitable for in vitro and in vivo studies, can also used for in vitro studies. |
| Tween 80 | Liquid, 100% | 12 mg/ml, 15 mg/ml if kept for long time (3-5 days) | Stable undiluted, stable after dilution in water or culture medium, PBS, precipitates slowly in saline. | Maximum solubility compared to any other solvent tested. Stable and remains clear upon dilution and suitable for both in vitro and in vivo studies. |
| Phosal 53 MCT (phospholipids) | Thick oily liquid | 10 mg/ml | Stable, clear, thick solution. Should be diluted in oils or phospholipids. Forms emulsion in water | Useful only for in vivo drug dosing |
| Phosal 50 PG (phospholipids) | Thick oily liquid, slightly thinner than Phosal 53 MCT | 10 mg/ml | Stable, clear, thick solution. Should be diluted in oils or phospholipids. Forms emulsion in water | Useful only for in vivo drug dosing. |
| Olive oil, canola oil, and coconut oil | Liquid, 100% | 5 mg/ml | Stable, should be diluted only in oils, forms emulsions in water | Not useful for in vitro studies; useful for in vivo drug dosing |

In vitro activity of CFM formulations according to the present invention was determined against CD, with all formulations exhibiting excellent activity (Table 19). MICs were similar to DMSO solubilized drug used in our in vitro studies.

sterilized. MIC of CFM was determined in culture medium containing 20% fecal extracts. No significant deviation in MIC was found. A one to two fold increase in MIC was demonstrated from experimental manipulations, as shown in Table 20 below:

TABLE 20

Effect of fecal extracts on the MIC of CFM against *C. difficile* VPI10463

| | MIC (μg/ml) | | | |
|---|---|---|---|---|
| | Expt. 1 | | Expt. 2 | |
| Drugs: | −fecal extract | +fecal extract | −fecal extract | +fecal extract |
| CFM | 0.125 | 0.5 | 0.062 | 0.125 |
| VAN | 0.5 | 1 | 0.5 | 0.5 |
| MET | 0.062 | 0.125 | 0.062 | 0.125 |

Human feces (20% w/v) was extracted in BHI broth, filter sterilized and used for testing MIC.

Drug dilutions prepared in the fecal extracts were incubated for 4 hrs in anaerobic incubator before adding bacterial suspension.

Figure 9:
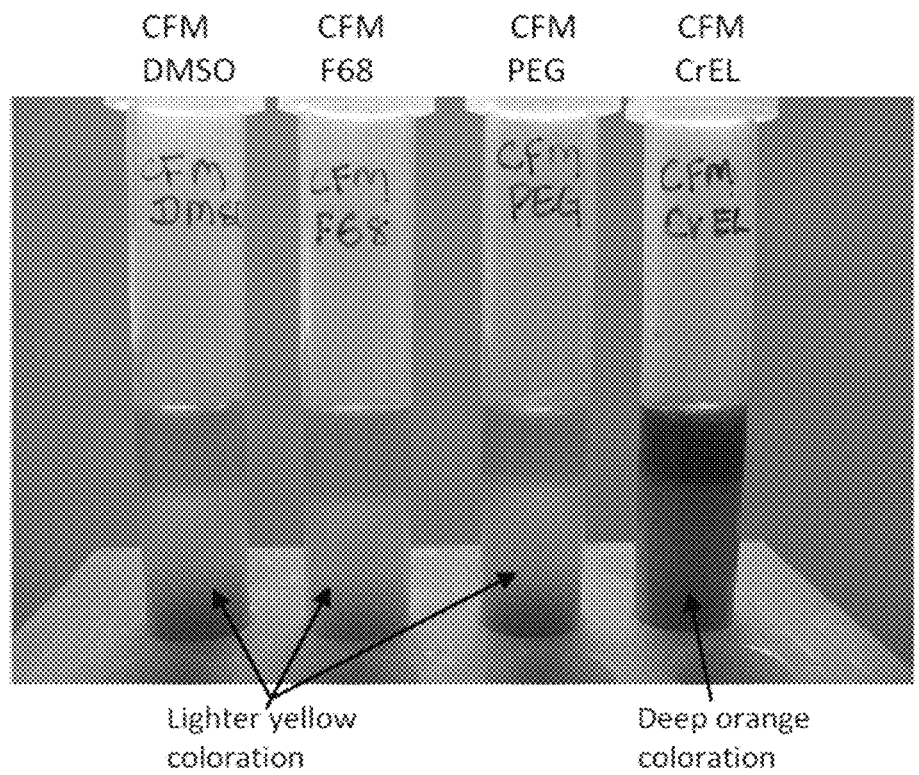
FIG. 9 is an image of sample vials of supernatants of CFM-DMSO, CFM-F68, CFM-PEG, and CFM CrEL formulations.
Figure 10:
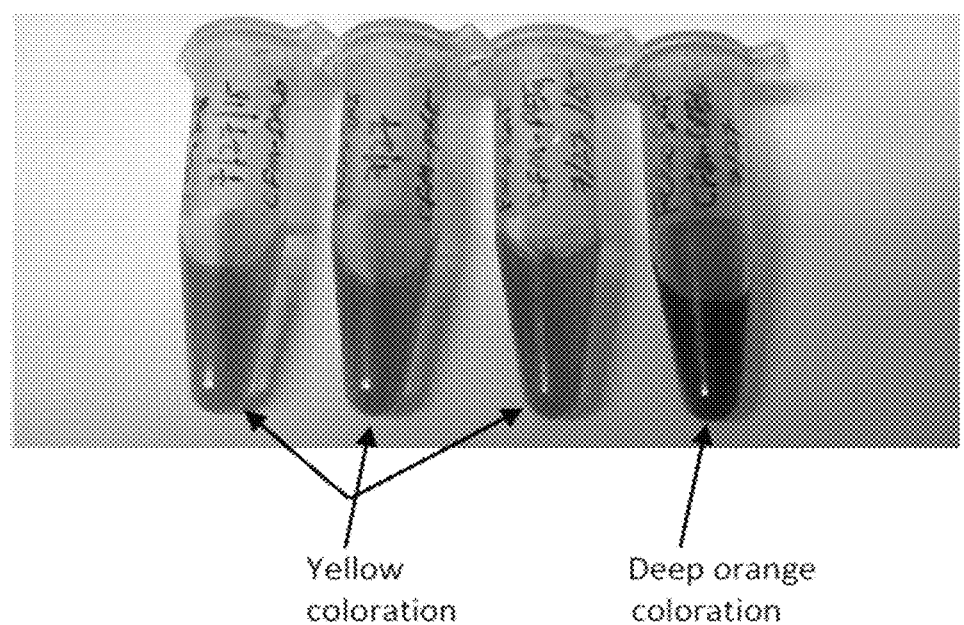
FIG. 10 is an image of the sample vials of the supernatants of FIG. 9 incubated with fecal extracts.

Subsequently, different CFM formulations (CFM-DMSO, CFM-F68, CFM-PEG and CFM-CrEL) were added to 2 ml volumes of 20% feces in BHI broth to give 128 μg/ml concentrations and incubated for 2 hours at 37° C. Upon centrifugation at 3000 rpm for 15 minutes, insoluble fecal matter pelleted at the bottom, leaving supernatant liquid phase on top. The supernatants of CFM-DMSO, CFM-F68 and CFM-PEG formulations were yellowish in color (FIG. 9 and FIG. 10), similar to BHI broth color, indicating most of the drug in these sample tubes pelleted along with particulate fecal matter leaving little or no drug in the liquid phase. In contrast, the supernatant of feces incubated with CFM-CrEL was deep orange in color (FIG. 9 and FIG. 10), suggesting the presence of drug in the liquid phase. Afterward, the supernatants were transferred into microcentrifuge tubes, spun at 5000 rpm for 10 minutes and filter sterilized through 0.45 μm followed by 0.22 μm filters. Even though some drug bound to the filter membrane, the supernatant of feces incubated with CFM-CrEL remained deep orange (FIG. 10), indicating the presence of soluble CFM.

The supernatants of feces incubated with the other three formulations remained yellowish, similar to the color of BHI broth. The MIC of the filtered supernatants was determined by a broth microdilution method against CD. CFM formulations prepared in BHI broth, without centrifugation and after centrifugation, served as controls (Table 21).

CFM formulations in DMSO, PEG and CrEL showed similar activity in BHI control with MIC of 0.0625 μg/ml (Table 21, column 1). Centrifugation of the CFM formulations prepared in BHI resulted in sedimentation of insoluble drug and reduction of MIC. The extent of reduction was highest for CFM-F68, followed by CFM-DMSO, CFM-PEG and CFM-CrEL, respectively (Table 21, column 2). Incubation of CFM-DMSO, CFM-F68 and CFM-PEG formulations with 20% feces resulted in binding of CFM to particulate matter in the feces with little or no drug in the liquid phase upon centrifugal separation and displayed no antibacterial activity, with MIC reaching >32 μg/ml. CFM-CrEL formulation, on the other hand, showed highest activity with MIC of 0.25 μg/ml (Table 21, column 3). Incubation in feces did not substantially affect the MIC of VAN, which exhibited only a 2-fold increase. However, MIC of MET increased significantly from 0.125 to >32 μg/ml. suggesting that MET also binds to particulate fecal matter, thereby causing a significant reduction in antibacterial activity.

TABLE 21

In vitro activity of CFM formulations following incubation with feces

| | MIC (μg/ml) in | | |
|---|---|---|---|
| Drug/formulation | BHI control* | Centrifuged BHI control** | Fecal extracts*** |
| CFM-DMSO | 0.062 | 1 | >32 |
| CFM-F68 | 0.25 | 32 | >32 |
| CFM-PEG | 0.062 | 0.5 | >32 |
| CFM-CrEL | 0.062 | 0.25 | 0.25 |
| VAN | 0.5 | 0.5 | 1.0 |
| MET | 0.062 | 0.125 | >32 |

MIC was determined by broth microdilution method in BHI broth against CD strain VPI 1063.
CFM = clofazimine;
DMSO = dimethyl sulfoxide;
F68 = Pluronic diblock polymer;
PEG = polyethylene glycol400;
CrEL = cremophor EL;
VAN = vancomycin;
MET = metronidazole.
*Serial drug dilutions were prepared in BHI tested for activity without centrifugation.
**Drugs were diluted in BHI to give 128 μg/ml concentration, incubated for 2 hr at 37° C., centrifuged at 5000 rpm for 10 min, supernatants were diluted serially and tested for activity.
***Drugs were diluted in 20% feces to give 128 μg/ml concentration, incubated for 2 hr at 37° C., centrifuged at 5000 rpm for 10 min, supernatants were filter sterilized, diluted serially and tested for activity.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A method for inhibiting the activity of *Clostridium difficile* in a subject, comprising administering to the subject a pharmaceutical composition consisting of clofazimine and at least one pharmaceutically acceptable excipient.

2. The method of claim 1, wherein the subject suffers from a *Clostridium difficile* associated disease or a *Clostridium difficile* infection selected from the group consisting of diarrhea, ulcerative colitis and Crohn's disease.

3. The method of claim 1, wherein clofazimine is administered in a concentration from 0.031 μg/mL to 1.0 μg/mL.

4. The method of claim 3, wherein clofazimine is administered in a concentration from 0.062 μg/mL to 0.25 μg/mL.

5. The method of claim 1, wherein the pharmaceutical composition is administered orally.

6. A method for inhibiting the activity of *Clostridium difficile* in a subject, comprising administering to the subject in need thereof a pharmaceutical composition consisting of clofazimine and at least one pharmaceutically acceptable excipient, wherein clofazimine is administered in a concentration from 0.031 μg/mL to 1.0 μg/mL.

7. A method for inhibiting the activity of *Clostridium difficile* in a subject, comprising administering to the subject a pharmaceutical composition consisting of clofazimine, at least one pharmaceutically acceptable excipient and at least one additional antimicrobial agent selected from the group consisting of metronidazole, vancomycin, and fidaxomicin.

8. The method of claim 7, wherein the subject suffers from a *Clostridium difficile* associated disease or a *Clostridium difficile* infection selected from the group consisting of diarrhea, ulcerative colitis and Crohn's disease.

9. The method of claim 7, wherein the administration of the at least one additional antimicrobial agent is concurrent.

10. The method of claim 7, wherein the administration of the at least one additional antimicrobial agent is sequential.

11. A method for inhibiting the activity of *Clostridium difficile* in a subject, comprising administering to the subject in need thereof a pharmaceutical composition consisting of clofazimine, at least one pharmaceutically acceptable excipient and at least one additional antimicrobial agent selected from the group consisting of metronidazole, vancomycin and fidaxomicin, wherein clofazimine is administered in a concentration from 0.031 µg/mL to 1.0 µg/mL.

\* \* \* \* \*